United States Patent
Kilpatrick et al.

(10) Patent No.: US 8,785,382 B2
(45) Date of Patent: Jul. 22, 2014

(54) LIPID THERAPY

(75) Inventors: Deborah Kilpatrick, Los Altos, CA (US); Syed Faiyaz Ahmed Hossainy, Fremont, CA (US); Irina Astafieva, Palo Alto, CA (US); Florian N. Ludwig, Mountain View, CA (US); Paul M. Consigny, San Jose, CA (US); Jeffrey T. Ellis, San Francisco, CA (US); Florencia Lim, Union City, CA (US)

(73) Assignee: Abbott Cardiovascular Systems Inc., Santa Clara ( * ) Notice: Subject to any disclaimer, the term of this patent is extended or adjusted under 35 U.S.C. 154(b) by 569 days.

(21) Appl. No.: 11/694,793

(22) Filed: Mar. 30, 2007

(65) Prior Publication Data

US 2007/0232539 A1 Oct. 4, 2007

Related U.S. Application Data

(60) Provisional application No. 60/789,049, filed on Apr. 3, 2006.

(51) Int. Cl.
- *A61K 38/00* (2006.01)
- *A61N 1/30* (2006.01)
- *A61M 31/00* (2006.01)

(52) U.S. Cl.
USPC .............................. 514/7.4; 604/19; 604/508

(58) Field of Classification Search
None
See application file for complete search history.

(56) References Cited

U.S. PATENT DOCUMENTS

| 5,911,698 | A  | * | 6/1999  | Cham ........................ 604/5.03 |
| 6,991,727 | B2 |   | 1/2006  | Bomberger et al. |
| 2003/0097173 | A1 |   | 5/2003  | Dutta |
| 2004/0106556 | A1 | * | 6/2004  | Zhu et al. ........................ 514/12 |
| 2004/0202711 | A1 | * | 10/2004 | Helmus et al. ................ 424/450 |
| 2005/0004004 | A1 |   | 1/2005  | Bellotti et al. |
| 2005/0019404 | A1 |   | 1/2005  | Sung et al. |
| 2005/0090444 | A1 |   | 4/2005  | Bellotti et al. |
| 2005/0133450 | A1 |   | 6/2005  | Bomberger et al. |
| 2005/0175666 | A1 |   | 8/2005  | Ding |
| 2006/0047336 | A1 |   | 3/2006  | Gale et al. |
| 2006/0172939 | A1 |   | 8/2006  | Bellotti et al. |

FOREIGN PATENT DOCUMENTS

| WO | Wo/2003/026492 | * | 4/2003 | ............. A61K 38/17 |
| WO | WO/2004/017946 | * | 3/2004 | |
| WO | WO-2004/017946 |   | 3/2004 | |
| WO | WO2005/070400  | * | 8/2005 | |

OTHER PUBLICATIONS

"How Are Stents Placed?", www.nih.gov/health/Diseases/stents/stents_placed.html, last viewed on Jul. 25, 2009).*

(Continued)

*Primary Examiner* — Alexander Kim
(74) *Attorney, Agent, or Firm* — Randy Shen, Esq.; Blakely Sokoloff Taylor & Zafman LLP

(57) ABSTRACT

A method including introducing into a blood stream a delipidated high density lipoprotein (HDL) and a bioactive agent. A composition including a delipidated high density lipoprotein (HDL) and an auxiliary agent in a form suitable for delivery into a blood vessel. A composition including Apo A1 comprising a hydrophobic ligand suitable to interact with cell surface binding sites. A composition including Apo A1 and an agent selected to one of increase the ATP-binding cassette protein 1 (ABCA1) transporter expression in macrophages and protect ABCA1 from thiol-mediated degradation.

18 Claims, 10 Drawing Sheets

(56) References Cited

OTHER PUBLICATIONS

Ischemic, www.thefreedictionary.com/ischemic, last viewed on Jul. 24, 2009.*
Systemic, www.askoxford.com/concise_oed/systemic?view=uk, last viewed on Jul. 22, 2009.*
Yang et al., Imaging of Vascular Gene Therapy., Radiology, 2003, vol. 228, pp. 36-49.*
Definition of "exogenous", obtained from Merriam-Webster online dictionary, last viewed Jul. 8, 2010, 2 pages.*
Lie, Desiree, Medscape Internal Medicine; Feb. 18, 2005; Cardiovascular Diagnostic and Treatment Options; pp. 1-6.*
Internal Medicine News, Oct. 1, 20056; New Treatments in Pipeline Raise HDL in Short, Long Term, p. 76.*
Zhu et al. PCT/US2003026709 (published on Apr. 3, 2004 as WO2004/017946).*
Kostner et al., HDL-therapy: the next big step in the treatment of atherosclerosis?, Future Cardiol., 2005, vol. 1, pp. 1-7.*
Stents (last viewed on Nov. 4, 2010), pp. 1-9.*
Sue Hughes (May 6, 2004) Heartwire; New Ideas on improving the functionality of HDL.*
Thomas Dayspring, High Density Lipoproteins Classification; last viewed on Jun. 5, 2013.*
Singh et al. Transport of fatty acids into human and rat peroxisomes. Differential transport of palmitic and lignoceric acids and its implication to X-adrenoleukodystrophy., J Biol Chem. (1992), vol. 267(19), pp. 13306-13313.*
Sinha et al., Permeation Enhancers for Transdermal Drug Delivery., Drug Development and Industrial Pharmacy, (2000), vol. 26(11), pp. 1131-1140.*
Koizumi et al., Behavior of human apolipoprotein A-I: phospholipid and apoHDL:phospholipid complexes in vitro and after injection into rabbits., J Lipid Res. (Nov. 1988), vol. 29(11), pp. 1405-1415.*
Lipostabil (last viewed on Jun. 6, 2013).*
Plasma Lipoproteins (last viewed on Jun. 7, 2013).*
Mithieux et al., Elastin, Advances in Protein Chemistry (2005), vol. 70, pp. 437-461.*
Rosinski-Chupin et al. SAGE analysis of mosquito salivary gland transcriptomes during Plasmodium invasion., Cell Microbiol. (2007), vol. 9(3), pp. 708-724.*
Gillotte, K. L., et al., "Removal of cellular cholesterol by pre-B-HDL involves plasma membrane microsolubilization", The Journal of Lipid Research, vol. 39, 1918-1928, Oct. 1998, Copyright 1998 by Lipid Research, Inc., (1998),23 pages.
Lewis, G. F., et al., "New Insights Into the Regulation of HDL Metabolism and Reverse Cholesterol Transport", Circulation Research, 2005;96:1221, (2005),27 pages.
Navab, M., et al., "An Apolipoprotien A-I Mimetic Works Best in the Presence of Apolipoprotein", Circ. Res. 2005;97; 1085-1086, (2005),3 pages.
Phillips, M. C., et al., "Mechanisms and consequences of cellular cholesterol exchange and transfer", 1987 Elsevier Science Publishers B.V.(Biomedical Division), (1987),53 pages.
Spady, D. K., "Reverse Cholesterol Transport and Atherosclerosis Regression", Circulation. 1999; 100:576-578; 1999 American Heart Association, Inc., (1999),6 pages.
Yarnell, A., et al., "Chewing the Fat about Cholesterol", Science & Technology, May 3, 2004, vol. 82, No. 18, pp. 30-31; From the ACS meeting, (2004),6 pages.
Abbott Cardiovascular Systems Inc., PCT International Preliminary Report on Patentability mailed Oct. 16, 2008; PCT/US2007/065791.
Abbott Cardiovascular Systems Inc., "PCT Search Report and Written Opinion," mailed Apr. 21, 2008, PCT/US2007/065791.
"PCT Invitation to pay Additional Fees; Annex to Form PCT/ISA/206; PCT/US2007/065791; Abbott Cardiovascular Systems Inc.; mailed Jan. 22, 2008".

* cited by examiner

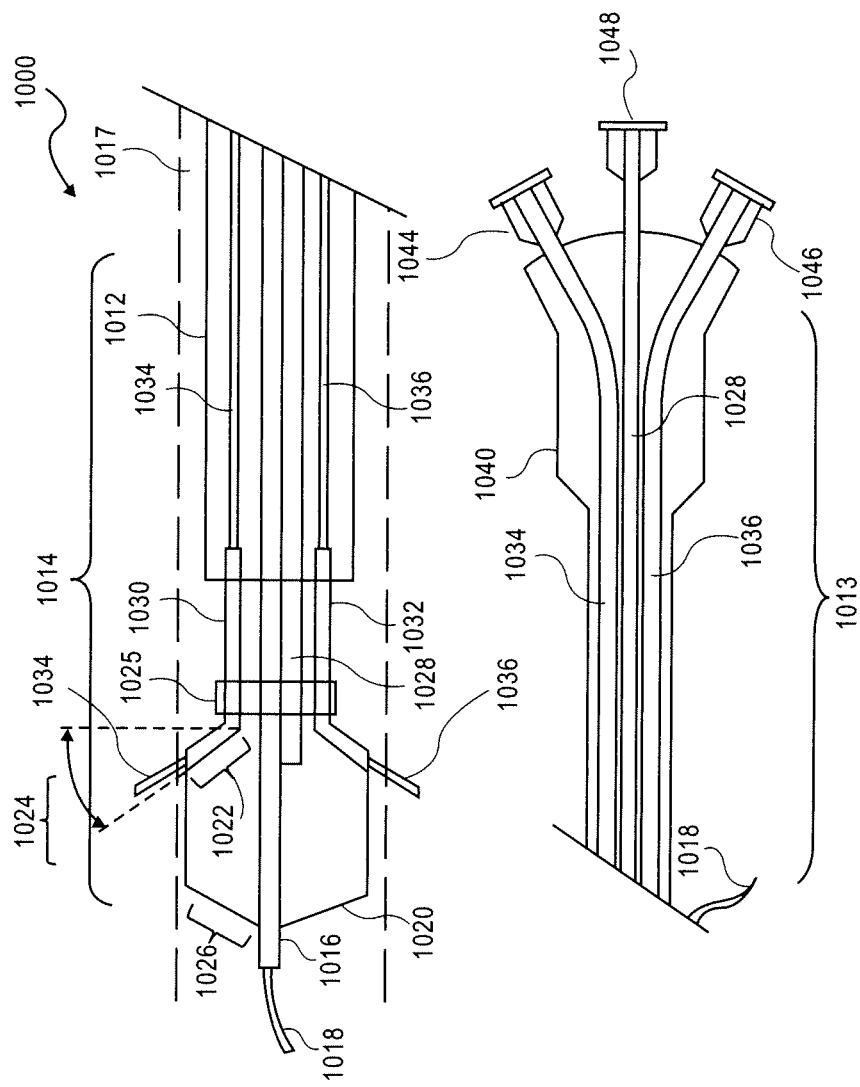

LIPID THERAPY

CROSS-REFERENCE TO RELATED APPLICATION

This application claims the benefit of the earlier filing date of U.S. Provisional Patent Application No. 60/789,049, filed Apr. 3, 2006, and incorporated herein by reference.

FIELD OF THE INVENTION

Compositions and methods for facilitating reverse cholesterol transport.

BACKGROUND OF THE INVENTION

Cholesterol is a major component of atherosclerotic plaque. Cholesterol accumulation within atherosclerotic plaque occurs when cholesterol influx into an arterial wall exceeds cholesterol efflux. Increased influx of cholesterol into the arterial wall is accompanied by an increased influx of monocytes/macrophages, which absorb oxidized aggregated low density lipoproteins (LDL) and store the cholesterol esters.

Current strategies to reduce coronary heart disease are primarily directed at reducing the influx of cholesterol into the arterial wall by lowering LDL cholesterol concentration. While lowering of plasma LDL levels offers some protection from coronary heart disease, the protection is not complete. As a consequence, there is an interest in strategies aimed at enhancing cholesterol efflux from the arterial wall and promoting its transport to the liver for excretion.

Cholesterol circulating in the blood is carried by plasma lipoproteins. Plasma lipoproteins are classified into groups according to size. Of these, the low density lipoprotein (LDL) and high density lipoprotein (HDL) are primarily the major cholesterol carrier proteins. The protein component of LDL, apolipoprotein B (Apo B), constitutes the atherogenic component. Apo B is not present in HDL. HDL includes apolipoprotein A-1 (Apo A1) and apolipoprotein A-2 (Apo A2) as well as other apolipoproteins.

Various forms of HDL have been described on the basis of electrophoretic mobility and include two major fractions: a first fraction with α-HDL mobility and another fraction referred to as pre-β HDL. Pre-β HDL is thought to be the most efficient HDL subclass for inducing cellular cholesterol efflux. Pre-β HDL fractions includes Apo A1, phospholipids and free cholesterol. Pre-β HDL are considered to be acceptors of cellular free cholesterol and are believed to transfer free and esterified cholesterol to α-HDL.

Two pathways have been proposed to describe the movement of cholesterol from a plasma membrane to acceptor particles such as pre-β HDL. In the "aqueous diffusion pathway," cholesterol molecules spontaneously desorb from cell membranes and are then incorporated into acceptor particles (pre-β HDL) after traversing the intervening aqueous space by diffusion. It is believed that the aqueous diffusion pathway does not require interaction with specific cell receptors.

The second model, referred to as the "microsolubilization pathway," involves the interaction of HDL (presumably an Apo A1 interaction) with a cell surface binding site. The HDL induces an intracellular signal leading to translocation of cholesterol from intracellular sites to the plasma membrane. The physiological acceptors or carriers for the translocated cholesterol are nascent HDL particles, including α-HDL and pre-β HDL.

Cholesterol that is transferred to nascent HDL particles is esterified by lecithin-cholesterol acyl transferase (LCAT) to cholesteryl esters. These esters are hydrophobic and tend to move into the core of the HDL particle. The HDL cholesteryl esters may return or be delivered to the liver and are excreted from the liver into bile, either directly or after conversion to bile cells.

It is believed that α-HDL and pre-β HDL particles, the primary acceptors or carriers for translocated cholesterol, do not occur in the same relative fractions as nascent HDL particle in the blood stream of an adult human. Thus, the carrier potential of each fraction is believed to be inversely proportional to its relative fraction of the total HDL quantity. In other words, the fraction with the highest carrier potential (pre-β HDL) occurs in the smallest overall amount in vivo.

SUMMARY OF THE INVENTION

The present invention relates to methods for improving the carrier potential of nascent HDL to accept cholesterol, particularly for improving reverse cholesterol transport by the aqueous diffusion pathway or the microsolubilization parthway. In one embodiment, the invention relates to a method whereby a delipidated high density lipoprotein (e.g., delipidated α-HDL) and a bioactive agent are introduced into a blood stream or tissue. An example of a bioactive agent includes an apolipoprotein A1 (Apo A1) or a mutant or mimic form thereof. Delipidated HDL, or apolipoprotein A1 (Apo A1) or a mutant or mimic form thereof, or a molecule mimicking the cholesterol transporting capacity of ApoA1, may be utilized to accept cholesterol, particularly cholesterol translocated from intracellular sites by way of the microsolubilization pathway or the aqueous diffusion pathway. The delipidated HDL and bioactive agent may be used to induce regression or impact (e.g., slow) progress of an atherosclerotic plaque.

The introduction of a delipidated HDL and a bioactive agent may be through a catheter system utilizing a systemic or local approach. Representatively, a local introduction may involve introducing the delipidated HDL and the bioactive agent to an ischemic area such as adjacent to or at an atherosclerotic plaque. Alternatively, the delipidated HDL and the bioactive agent may be introduced upstream from a treatment site. A further alternative is the introduction of the delipidated HDL and the bioactive agent locally into a blood vessel or beyond, such as introduction into a periadventitial area.

In another embodiment, the invention relates to a method whereby an amount of blood is withdrawn from a patient, HDL present in the withdrawn blood is delipidated, and the delipidated HDL is returned to the patient. This may be accomplished using a closed loop system where a single catheter assembly withdraws the blood and returns the delipidated HDL back into a blood vessel of a patient. Alternatively, separate assemblies may be used to withdraw the blood and return the delipidated HDL.

In another embodiment, the invention relates to a composition capable of improving the carrier potential of nascent HDL to accept cholesterol, wherein the composition comprises a delipidated HDL and an auxiliary agent in a form suitable for delivery into a blood vessel. The auxiliary agent, in one embodiment, has a property that will enhance the residence time of the HDL at a specific location within a blood vessel, such as adjacent to or at an atherosclerotic plaque. Alternatively and/or additionally, the auxiliary agent may have a property that will stabilize an amphipatic helical structure of the HDL in situ. Still further, the auxiliary agent may include a property that will enhance the interaction between Apo A1 and cell surface binding sites or that will increase the solubility of free cholesterol and phospholipids in fully lipidated high density lipoproteins.

In another embodiment, a composition according to an embodiment of the invention comprises delipidated HDL and an auxiliary agent where the auxiliary agent includes a cross-linker of Apo A1 such as a synthetic or naturally occurring cross-linker. Examples include, but are not limited to, lysoylperoxidate, gennicin, and reuterin, as well as other aldehyde-containing molecules. The cross-linked or ligated Apo A1 may enhance its binding during the microsolubilization pathway and/or enhance the diffusion of phospholipids during the aqueous diffusion pathway.

In another embodiment, a composition includes a mutant of Apo A1 including a hydrophobic ligand suitable to interact with cell surface binding sites. Such mutant will enhance the binding of Apo A1 for the microsolubilization pathway and/or the diffusion of phospholipids for the aqueous diffusion pathway.

In a further embodiment, a composition comprising Apo A1 and an agent that will increase the ATP-binding cassette protein1 (ABCA1) transporter expression and macrophages and/or protect ABCA1 from thiol-mediated degradation is described.

Additional features, embodiments, and benefits will be evident in view of the figures and detailed description presented herein.

BRIEF DESCRIPTION OF THE DRAWINGS

Features, aspects, and advantages of embodiments will become more thoroughly apparent from the following detailed description, appended claims, and accompanying drawings in which:

FIG. 10 shows a schematic cross-sectional side view of another embodiment of a catheter assembly in a blood vessel.

FIG. 11 shows a cross-sectional side view of a needle suitable for use in the catheter assembly in FIG. 10.

DETAILED DESCRIPTION OF THE INVENTION

The following embodiments describe techniques and devices directed, in one aspect, at improving reverse cholesterol transport by the aqueous diffusion pathway or the microsolubilization parthway.

Figure 1:
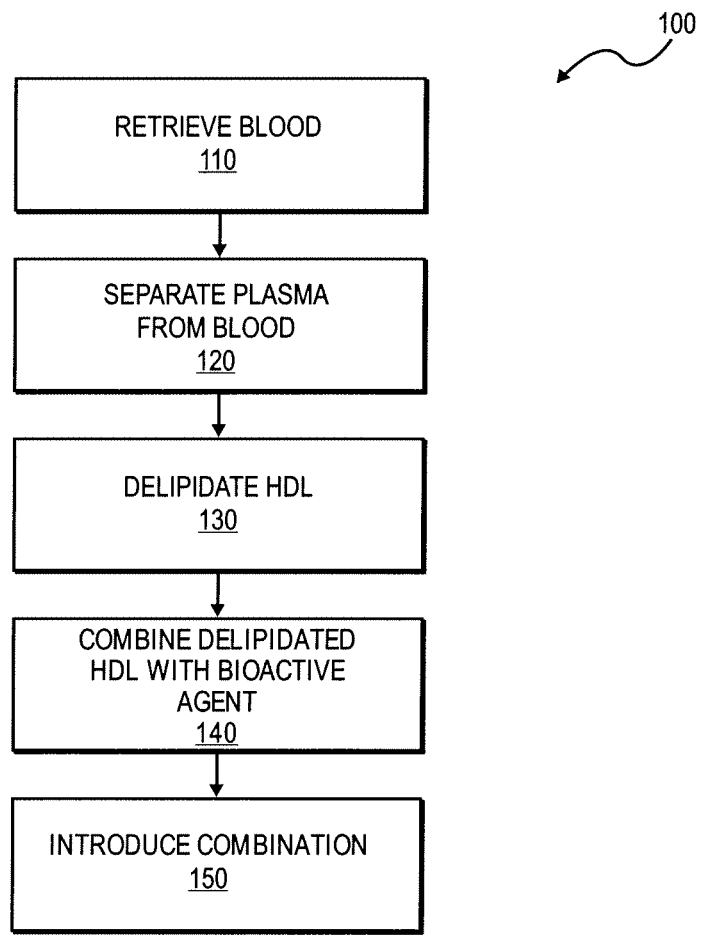
FIG. 1 shows a flow chart of a process for delipidating HDL from a sample of blood and infusing the delipidated HDL, which may further include an adjuvant.

FIG. 1 shows a process scheme for delipidating HDL (e.g., α-HDL) from blood plasma and introducing the delipidated HDL into the blood with or without an adjuvant, such as Apo A1 or a mutant or mimic thereof. The technique, in one embodiment, enhances the carrier potential of nascent HDL available to accept cholesterol, particularly cholesterol translocated from intracellular sites by way of the microsolubilization pathway. Referring to FIG. 1, process 100 describes a method of retrieving blood from a patient (block 110) and then separating plasma from the blood (block 120). The plasma may be separated from the blood by known techniques, such as filtration or centrifugation. The separated plasma will typically contain LDL and HDL.

Following separating plasma from the blood, the HDL may be delipidated (block 130). One method to delipidate HDL is through a solvent process. Representatively, the plasma may be mixed with a solvent or solvents. In one embodiment, a solvent system is designed to reduce lipid levels of HDL selectively while lipid levels of LDL remain substantially intact. Factors such as the solvent or solvents employed, mixing methods, time and temperature may vary. Suitable solvents include, but are not intended to be limited to, aromatic, aliphatic, or alicyclic hydrocarbons, ethers, phenols, esters, alcohols, halohydrocarbons, and mixtures thereof.

Suitable hydrocarbons may be linear, branched or cyclic, saturated or unsaturated. In another embodiment, suitable hydrocarbons include, but are not limited to, $C_5$ to $C_{20}$ aliphatic hydrocarbons such as petroleum ether, hexane, heptane and octane; haloaliphatic hydrocarbon such as chloroform, 1,1,2-trichloro-1,2,2-trifluoroethane, 1,1,1-trichloroethane, trichloroethylene, tetrachloroethylene, dichloromethane and carbon tetrachloride; thioaliphatic hydrocarbon; perfluorocarbons such as perfluorocyclohexane, perfluoromethylcyclohexane, and perfluorodimethylcyclohexane; fluoroethers such as sevoflurane; aromatic hydrocarbons such as benzene; and alkylarenes such as toluene, haloarenes, haloalkylarenes and thioarenes. Other suitable solvents may include saturated or unsaturated heterocyclic compounds such as derivatives of pyridine and aliphatic, thio or halo derivatives thereof, and perfluorooctyl bromide. Another suitable solvent may be perfluorodecalin.

Suitable esters that may be used include, but are not limited to, ethyl acetate, propyl acetate, butyl acetate and ethyl propionate. Suitable ketones which may be used as a solvent include, but are not limited to, methyl ethyl ketone.

In one embodiment, suitable alcohols include those alcohols that are not appreciably miscible with plasma or other biological fluids. Suitable alcohols include $C_1$-$C_8$ containing alcohols, particularly when used in combination with another solvent. Exemplary alcohols include, but are not limited to, butanols, pentanols, hexanols, heptanols and octanols, including iso forms thereof Often the choice of alcohol will depend on a second solvent employed. In one embodiment, lower alcohols are combined with lower ethers.

Suitable ethers for use as a solvent, include but are not limited to, $C_4$-$C_8$ ethers such as ethyl ether, diethyl ether and propyl ether, including but not limited to, di-isopropyl ether (DIPE). Combinations of ethers, such as DIPE and diethyl ether, are also contemplated. In another embodiment, combinations of ethers and alcohols are employed, such as DIPE and butanol. In another embodiment, combinations of fluoethers and alcohols are employed, such as sevolfurane and butanol.

In one embodiment, a solvent process employs a solvent system with a range solubility parameter value. The solubility parameter of the solvent system will be adjusted by using one or more polar organic solvents with one or more apolar solvents. Examples of polar solvents include, but are not limited to, acetone, tetrahydrofuran (THF), dimethylformamide (DMF), dimethylacetamide (DMAC), isopropyl alcohol (IPA), and octanol. Examples of apolar (nonpolar) solvents include, but are not limited to, fluorinated solvents, hexane, heptane and cottonseed oil. The solvent system can be selected such that it is miscible with the plasma (which is aqueous).

A surfactant may be combined with the solvent and lipoprotein. Suitable surfactants include, but are not limited to, sulfates, sulfonates, phosphates (including phospholipids), carboxylates and sulfosuccinates. Certain anionic amphilic materials may also be useful, including, but are not limited to, sodium dodecyl sulfate (SDS), sodium decyl sulfate, bis-(2-ethylhexyl) sodium sulfosuccinate (AOT), cholesterol sulfate and sodium laurate. Alternatively, other amphiphilic micelle- or bilayer-membrane-forming molecules may be useful, including but not limited to amphiphilic block co-polymers and sphingolipids.

In one embodiment, the plasma and solvent(s) are mixed, agitated, or otherwise intimately contacted. Suitable mixing methods include, but are not limited to, an in-line static mixer, a rotating flask, a vortexer, a centrifuge, a sonicated flask, a high shear tube, a homogenizer, a blender, hollow fiber contactor, a centrifugal pump, a shaker table, a swirling process, a stirring process, an end-over-end rotation of a sealed container, and the like, or any combination of these devices or processes. The amount of time required for adequate mixing will vary depending on the solvent and mixing method employed. Simple mixing times may vary from about one second to about 24 hours. For example, gentle stirring and end-over-end rotation mixing may be employed from about one second to about 24 hours; vigorous stirring and vortexing for a period of one about second to about 30 minutes; swirling for a period of about one second to about two hours; and homogenization for a period of about one second to about ten minutes.

In one embodiment, a suitable temperature for a mixing of solvent and plasma is selected so as to avoid denaturing the plasma. A representative temperature is at or about 37° C. or less.

Figure 2A:
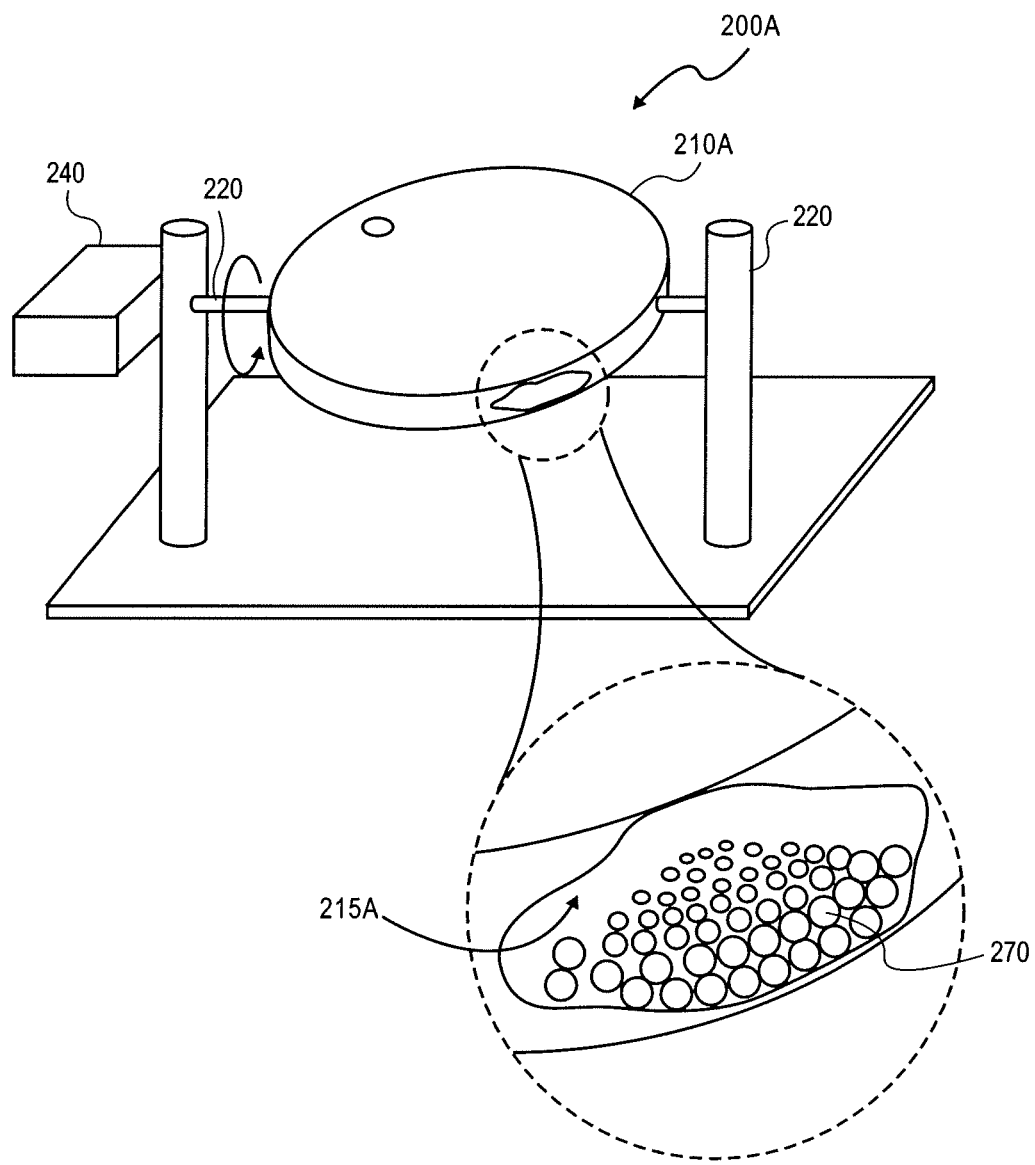
FIG. 2A shows a schematic, top perspective view of an embodiment of a delipidation sub-module.

FIG. 2A shows a top perspective view of a delipidation sub-module that may be used, for example, for selective delipidation of HDL (e.g., α-HDL) from plasma. In this embodiment, delipidation sub-module 200A includes canister 210A that may contain a suitable solvent and blood plasma. In one embodiment, canister 210A has a disk-like shape that is mounted on spindle 220. Optional motor 240 (e.g., an electric motor) is connected to spindle 220 and may rotate spindle 220. Alternatively, spindle 220 may be rotated by hand.

The disk-like shape of canister 210A will tend to maximize the surface area of contact and increase solid-liquid leaching efficiency (i.e., the extraction of lipid and cholesterol from HDL by the solvent). In one embodiment, a process of delipidating HDL from blood plasma contained in canister 210A is a semi-batch process because fresh solvent may be introduced to improve the efficiency of the extraction. The efficiency of the extraction process will reduce the size of the canister and the time of the extraction process.

In one embodiment, canister 210A includes hollow, otherwise empty volume 215A that may be filled either partially or totally with a mixture of plasma and solvent. In another embodiment, a portion of volume 215 of canister 210A may be loaded with a particulate such as a porous particulate. The inset of FIG. 2A shows particulate 270 within volume 215A of canister 210A. In one embodiment, particulate 270 may be coated with an antibody specific for Apo A1 or another component of HDL that, relative to other components of the plasma, is unique to HDL to specifically target the HDL molecule. A representative example of a material for particulate 270 is activated carbon particles having an average particle diameter on the order of 5 to 100 microns and an average porosity of 30 to 70 percent (volume fraction of pore). In this example, the pores may be coated with an antibody specific for Apo A1, such as aPL (anti-2glycoprotein-1) antibodies. According to one process, a plasma may be introduced in the canister 210A and decanted off followed by the introduction of solvent into the canister for delipidation. The trapped (bound) HDL will tend to be delipidated upon exposure to the solvent.

Figure 2B:
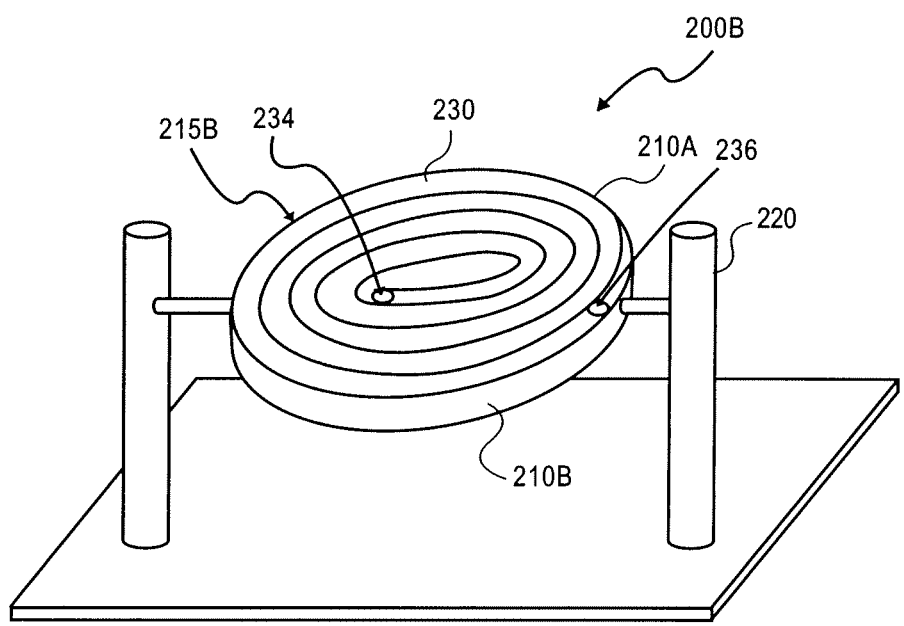
FIG. 2B shows a schematic, top perspective view of another embodiment of a delipidation sub-module.

FIG. 2B shows another embodiment of a delipidation sub-module that may be used, for example, for selected delipidation of HDL (e.g., α-HDL) from plasma. In this embodiment, delipidation sub-module 200B includes canister 210B having volume 215B. Canister 210B has a disk-like shape that may be mounted on a spindle, such as spindle 220 in FIG. 2A.

FIG. 2B shows canister 210B with a top side removed. Disposed within volume 215B of canister 210B, in one embodiment, is tube 230 wrapped in a coiled configuration. In one embodiment, the interior walls of tube 230 are coated with an antibody specific for Apo A1 or another component of HDL that, relative to other components of plasma, is unique to HDL to specifically target the HDL molecule. Thus, coiled tube 230 may serve to specifically immobilize HDL on the surface similar to the principal of affinity chromatography. The degree of coiling in the diameter of a lumen of tube 230, the surface density of antibody dictates the efficiency of separation as extrinsic variables, while the affinity to antibody serves as the intrinsic manipulatable variable. In another embodiment, a coiled tube, such as tube 230 within canister 210B is coated with antibody specific for HDL (e.g., Apo A1) as described with reference to FIG. 2B, and tube 230 is also loaded with porous particulate. By combining a porous particulate with a lumen coated with antibody, increased separation of HDL may be achieved.

Plasma may be introduced into canister 210B and into tube 230 through opening 234. The plasma travels through tube 230 and exits tube 230 and canister 210B at opening 236. Tube 230 containing antibodies specific for HDL and optionally porous particulate separates the HDL molecules from the plasma. Following separation of the HDL, a solvent may be added to canister 210B (e.g., solvent added to tube 230) to delipidate the HDL.

In another embodiment, a canister such as canister 210A of FIG. 2A may be loaded with a porous particulate to increase the contact area between solvent and plasma. This concept is similar to fluidized bed techniques for efficient mass transport. In this embodiment, the selection of particulate will be such that adverse effects such as protein denaturation, depletion of proteins and release of contaminates is minimized. Examples of materials that may be used in particulate form include, but are not limited to, ethylene vinyl alcohol (EVA), polyethylene glycolated polystyrene, polyacrylnitrile (PAN) or polyethylene glycolated PAN, or polysulfone (PS). The particulate may be spherical or another shape such as discoid, random ship, thin slabs, etc.

In another embodiment, particulate 270 may be coated with, or have adsorbed or conjugated to their surface, molecules having an affinity for cholesterol higher than the HDL complex, or the Apo A1 protein. For example, cyclodextrins and more specifically beta-cyclodextrins may be used to delipidate HDL in this fashion. If particulate 270 is a porous particulate, the pores of the particulate may be coated with as well. The delipidated HDL may be easily separated from the cholesterol bound to the particulate. Alternatively, or additionally, the plasma may be run through a column packed with particulate such as described above. Upon contact with the surface of the particulate, cholesterol will be bound by the coated surface of the particulate and the delipidated plasma will exit from the column.

In one embodiment, a canister such as canister 210A including a porous particulate may be loaded with blood plasma and solvent to delipidate HDL. The canister may be rotated and tumbled for complete mixing. A disk configuration, such as shown in FIG. 2A, will tend to maximize the surface area of contact and increase the solid-liquid leaching efficiency (extraction of lipids and cholesterol from HDL by solvent). In one embodiment, the process may be described as a semi-batch process because fresh solvent can be introduced to improve the efficiency of extraction.

The combination of the solvent and the plasma with mixing will tend to remove lipids from HDL present in the plasma. Following adequate removal of lipids from HDL, the solvent may be separated from the plasma by various techniques. One technique involves settling the combined solution so that the mixture separates into a first layer and second layer. The first layer will include a mixture of solvent and lipid that has been removed from HDL particles. The second layer will include a mixture of residual solvent, delipidated HDL particles and other elements of the input fluid (e.g., LDL particles). The first layer may be separated from the second layer and then a further solvent removal operation may be performed to remove residual solvent from the second layer. Representatively, the residual solvent may be removed by passing the solution consisting of the second layer through a charcoal column selected to remove the specific solvent used in the delipidation process. Alternatively or additionally, evaporation techniques or hollow fiber contactors may be utilized to remove solvent.

Following delipidation or prior to delipidation, the amount of LDL cholesterol may be reduced from the plasma. Methods for extracting LDL from plasma include centrifugation and filtration.

Following the delipidation of HDL, the delipidated HDL may be modified. One such modification is adding a surface coating to the delipidated HDL to increase the partition coefficient (i.e., the specificity of uptake) of the delipidated HDL into an atheromatous lesion. Increasing the partition coefficient will tend to enhance the movement of cholesterol by the microsolubilization pathway. Representative examples of suitable surface coatings include, but are limited to, thiolated chitosan, tridodecyl methyl ammonium chloride (TDMAC), phospholid, phyethylene glycolated phospholipid, aptamer coating, etc.

In another embodiment, delipidated HDL may be modified by encapsulating the delipidated HDL in a liposome according to methods known in the art, or by complexing the delipidated HDL with phospho- or sphingolipids. Liposome encapsulation or lipid complexation will also tend to increase the partition coefficient (i.e., the specificity of uptake) of the delipidated HDL into an atheromatous lesion. Encapsulation in a liposome may be achieved by agitating a phospholipid film such as dimyristoylphosphatidylcholine (DMPC) in an aqueous suspension of delipidated HDL. Alternatively, liposomes may be pre-formed and then the pre-formed liposomes mixed with delipidated HDL. Encapsulation will tend to take place due to the fusion and subsequent inclusion of HDL into the pre-formed liposome.

Referring again to FIG. 1, following the delipidation of HDL and optional modification, the plasma containing delipidated HDL may be introduced (e.g., infused) into a patient (block 150). In one embodiment, the plasma containing the delipidated HDL is combined with a bioactive agent (block 140). One suitable bioactive agent is Apo A1 or mutant thereof (e.g., Apo A1 milano peptide), or an Apo A1 mimetic peptide. In another embodiment, the bioactive agent may additionally or alternatively be, but is not limited to, an anti-inflammatory or drug (bisphosphonate, clobetasol) or an immunomodulator (e.g., everoliumus). The plasma and bioactive agent are introduced into a patient, in one embodiment, to enhance the microsolubilization pathway (block 150). As noted above, Apo A1 is believed to interact with cell surface binding sites, thus inducing an intracellular signal leading to translocation of cholesterol from intracellular sites to the plasma membrane in the microsolubilization pathway. Thus, the introduction of Apo A1 will tend to increase the translocation of cholesterol from a plasma membrane. At the same time, the introduction of delipidated HDL will tend to increase the carrier potential of nascent HDL. The delipidated HDL, particularly delipidated α-HDL, in combination with pre-β HDL, will tend to increase the availability of carriers for the cholesterol translocated from a plasma membrane. It is believed that Apo A1 and delipidated plasma work synergistically, in that the translocation of cholesterol by Apo A1 is improved when Apo A1 is combined with a delipidated plasma.

In one embodiment, the delipidated HDL and optional bioactive agent (e.g., Apo A1) may be introduced systemically or locally via a catheter. In an alternative embodiment, a concentrated formulation of delipidated HDL with or without a bioactive agent may be introduced locally on, for example, an implantable scaffold (e.g., a stent) at a treatment site, such as at a location including adjacent (e.g., near) an atherosclerotic plaque.

Figure 3:
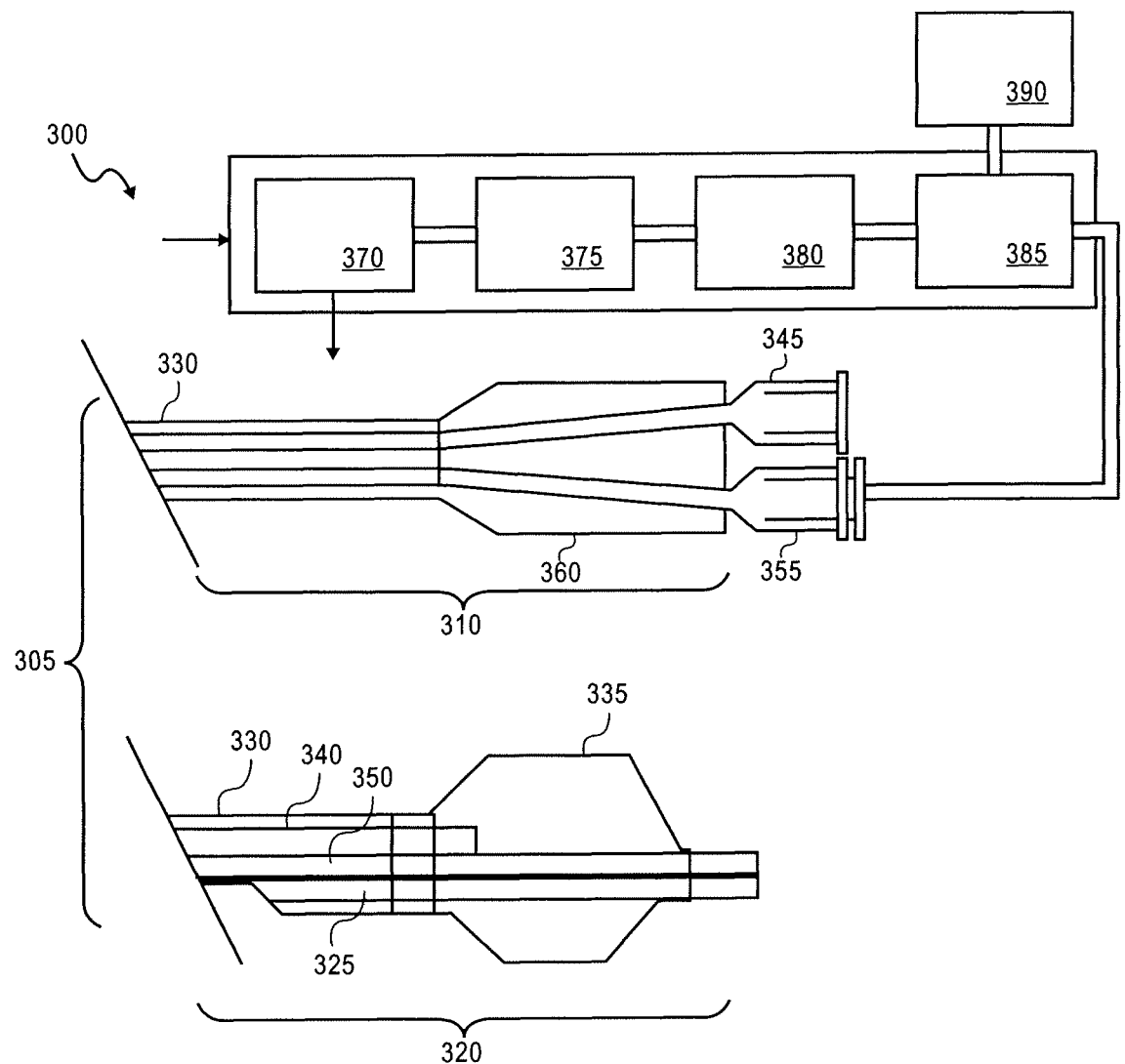
FIG. 3 shows a schematic cross-sectional side view of a system for delipidating HDL and introducing the delipidated HDL, which may further include an adjuvant.

In one embodiment, a therapy system is contemplated. FIG. 3 shows system 200 that permits withdrawal of patient blood plasma and implementation of selective delipidation of HDL (e.g., α-HDL) by a modular device that may be an attachment to a local delivery catheter. Referring to FIG. 3, system 300 includes a local delivery catheter assembly, in this case, including proximal portion 310 and distal portion 320. Distal portion 320 is intended to be inserted into a patient, such as inserted through a femoral or radial artery and advanced, typically over a guidewire and possibly through a guiding catheter, to a region of interest such as a coronary artery.

Catheter assembly 305 includes guidewire cannula 325 for allowing catheter assembly 305 to be fed and maneuvered over a guidewire (not shown). In one embodiment, guidewire cannula 325 extends the length of the catheter body from proximal portion 310 to distal portion 320. Representatively, in a typical procedure, a guidewire may be initially placed through a region of interest in a physiological lumen (e.g., a blood vessel) and catheter assembly 305 is advanced on/over the guidewire to or through a region of interest in an over the wire (OTW) fashion. In another embodiment, illustrated in FIG. 3, catheter assembly 305 is a rapid exchange (RX) type catheter assembly and only a portion of catheter assembly 305 (a distal portion) is advanced over the guidewire. It is appreciated that the guidewire may be retracted or removed once catheter assembly 305 is placed at a region of interest.

Catheter assembly 305 includes primary cannula or tube 330 that extends from proximal portion 310 of catheter assembly 305 to distal portion 320. Disposed within a lumen of primary cannula 330 are inflation cannula 340 and delivery cannular 350. Each of inflation cannula 340 and delivery cannula 350 extends from a proximal end of catheter assembly 305 to distal portion 320. At proximal portion 310 of catheter assembly 305, inflation cannula 340 is accessed at port 345 and delivery cannula 350 is accessed at port 355. In FIG. 3, each port is illustrated with a lure fitting for syringe attachment. Inflation cannula 340 and delivery cannula 350 extend from port 345 and port 355, respectively, through hub 360 into a lumen of primary cannula 330. In one embodiment, each of hub 360, port 345 and port 355 are intended to be positioned outside a patient (extracorporeal) when catheter assembly 305 is positioned at a region of interest within a blood vessel of a patient.

In the embodiment shown in FIG. 3, catheter assembly 305 includes balloon 335 incorporated at distal portion 320 of catheter assembly 305. Balloon 335 is an expandable body in fluid communication with inflation cannula 340. Inflation cannula 340 extends from inflation port 345 located at a proximal end of catheter assembly 305 through primary cannula 330 to a point within balloon 335.

In the embodiment shown in FIG. 3, balloon 335 is in an expanded or inflated state. Balloon 335 is selectively inflatable to dilate from a collapsed configuration to a desired and controlled expanded configuration. Balloon 335 can be selectively inflated by supplying a fluid (e.g., a liquid) into inflation cannula 340 at a predetermined rate of pressure through inflation port 345. Likewise, balloon 335 is selectively deflatable to return to a collapsed configuration or a deflated profile by withdrawing fluid through inflation port 345.

In one embodiment, balloon 335 is connected to a distal end of primary cannula 330 by an adhesive and/or a thermal bond. A distal end of balloon 335 is connected to each of delivery cannula 350 and guidewire cannula 325 by an adhesive and/or thermal bond.

In the embodiment shown in FIG. 3, system 300 includes a delipidation module that may be connected to delivery port 355 to supply, in one embodiment, delipidated HDL to delivery cannula 350. In the embodiment shown, the delipidation module includes filter sub-module 370 to separate plasma from a blood sample, delipidation sub-module 375 to delipidate HDL contained within a separated plasma, separation sub-module 380 to separate out the solvent, including the solvent containing lipids; and staging sub-module 385 to deliver delipidated HDL through delivery port 355 into delivery cannula 350. In one embodiment, a process is contemplated wherein blood may be withdrawn from a patient, perhaps at a site separate from the point of entry into the patient of catheter assembly 305. The withdrawn blood is introduced into filter sub-module 370 where the plasma is separated from the blood. The plasma may be sent to delipidation sub-module 375 while the remaining constituents of the blood (e.g., red blood cells, white blood cells, and other blood components) may be collected and optionally returned into the blood stream of the patient. Delipidation sub-module 375 may delipidate HDL through a solvent process such as described above wherein the plasma is combined with a solvent and mixed under appropriate conditions to delipidate HDL selectively. In one embodiment, delipidation sub-module 375 is a device such as described with reference to FIG. 2 and the accompanying text, including a disk-shaped canister with or without a particulate therein. The solvent including solvent containing lipids may then be separated in separation sub-module 380, for example, phase separation, charcoal adsorption, evaporation, and/or hollow fiber contactors (HFCs).

Delipidated HDL may be contained within staging sub-module 385 for delivery through delivery cannula 350 to a treatment site. In one embodiment, system 300 also includes adjuvant module 390. Adjuvant module 390 may contain an adjuvant, such as Apo A1 or a mutant form thereof and/or bioactive. Alternatively or additionally, adjuvant module 390 may include additional treatment agents, such as cellular components and drugs that may be beneficial to treating, for example, atherosclerotic plaque.

Figure 4:
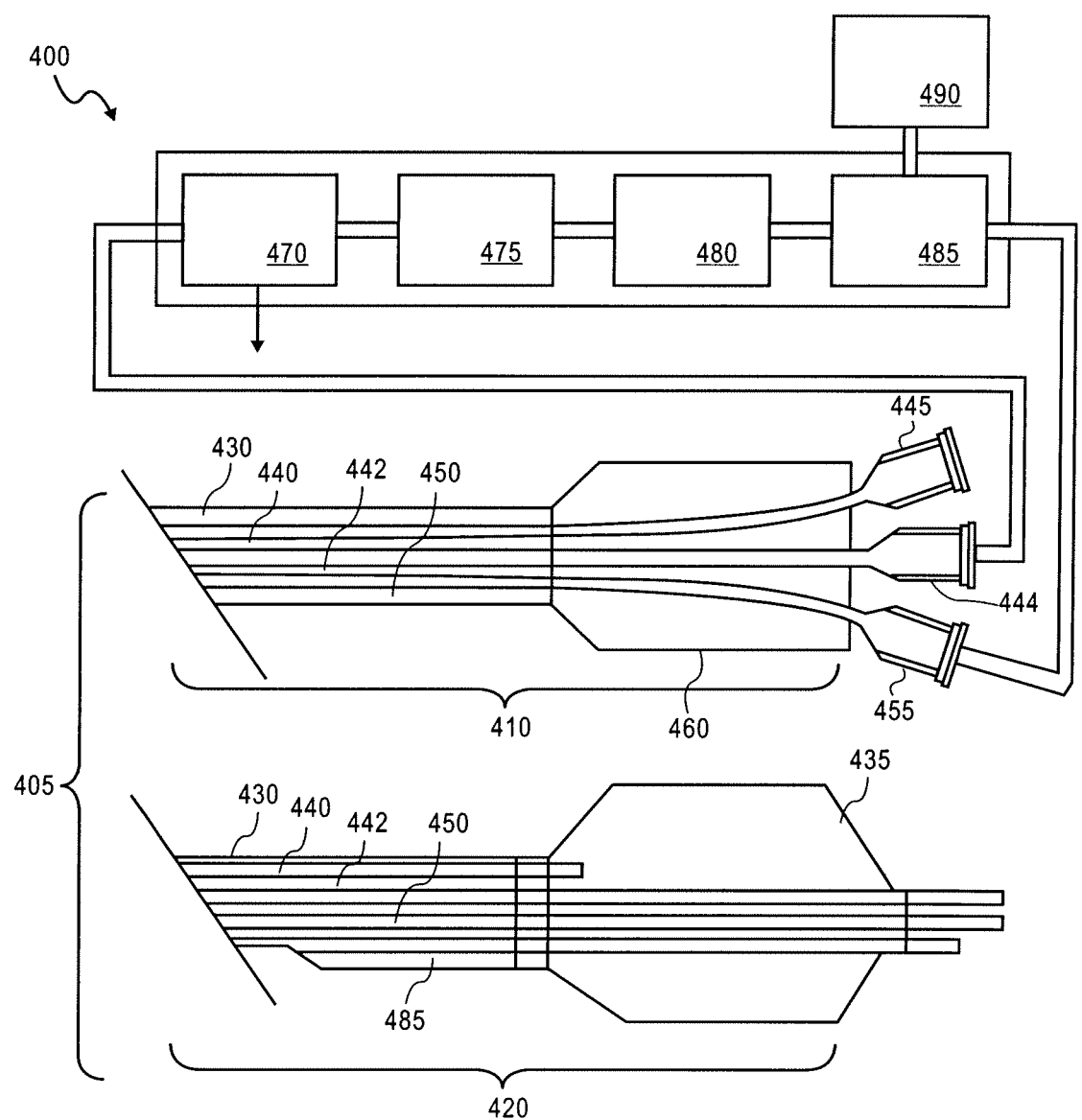
FIG. 4 shows a schematic cross-sectional side view of a system for withdrawing blood and implementing delipidation of HDL and introducing the delipidated HDL, which may further include an adjuvant.

FIG. 4 shows another embodiment of a therapy system. FIG. 4 shows system 400 that permits withdrawal of patient blood plasma and implementation of selected delipidation of HDL (e.g., $\alpha$-HDL) by a modular device that may be an attachment to a local delivery catheter. Referring to FIG. 4, system 400 includes a local delivery catheter, in this case including proximal portion 410 and distal portion 420. Distal portion 420 is intended to be inserted into a patient, such as inserted through a femoral or radial artery and advanced to a region of interest such as a coronary artery. Catheter assembly 405 includes guidewire cannula 425 for allowing catheter assembly 405 to be fed and maneuvered over a guidewire (not shown). An RX type catheter assembly is shown. In another embodiment, catheter assembly 405 may be an OTW type catheter assembly.

Catheter assembly 405 includes primary cannula or tube 430 that extends from proximal portion 410 of catheter assembly 405 to distal portion 420. Catheter assembly 405 also includes balloon 435 connected to a distal portion or end of primary cannula 430. Balloon 435 is shown in an expanded or inflated state. Balloon is inflated through the introduction of a liquid (e.g., fluid) through inflation cannula 440 disposed within a lumen of primary cannula 430. Thus, inflation cannula 440 extends from a proximal and of catheter assembly 405, through primary a lumen of primary cannula 430 to a point within balloon 435.

Disposed within a lumen of primary cannula 430, in this embodiment, are inflation cannula or tube 440, withdrawal cannula or tube 442 and delivery cannula or tube 450 each having a lumen therethrough. The description of a cannula as "withdrawal cannula" or "delivery cannula" is for purposes of explanation of this particular embodiment only and is not intended to limit the functionality of a particular cannula. In this embodiment, withdrawal cannula 442 and delivery cannula 450 each extends from a proximal end of catheter assembly 405 to a distal end extending beyond balloon 435. At a proximal end of catheter assembly 405 each of withdrawal cannula 444 and delivery cannula 455 are connected to delivery port 444 and delivery port 455, respectively. Inflation cannula 340 is connected to inflation port 445.

In the embodiment in FIG. 4, system 400 includes a delipidation module that may be connected to each of withdrawal port 444 and delivery port 455 of catheter assembly 405. In one embodiment, where catheter assembly 405 is placed within a blood vessel of a patient, blood is withdrawn through withdrawal cannula 442, through port 444 and delivered to the delipidation module. The withdrawal may be accomplished with or without mechanical aid (e.g., a pump). The delipidation module includes filter sub-module 470, delipidation sub-module 475, separation sub-module 380 and staging sub-module 485 connected in a series relationship. The withdrawn blood is introduced into filter sub-module 470 where the plasma is separated from the blood. Following filtration or separation, the plasma may be sent to delipidation sub-module 475 while the remaining constituents of the blood may be collected and possibly returned into the blood-stream of the patient. Delipidation sub-module 475 (e.g., such as described with reference to FIG. 2 and the accompanying text) may delipidate HDL (e.g., $\alpha$-HDL) through a solvent process such as described above wherein the plasma is combined with a solvent and mixed under appropriate conditions to delipidate HDL selectively. The solvent including solvent containing liquids may then be separated in separation sub-module 480 by a process such as one or more phase separation, charcoal adsorption, evaporation, and/or hollow fiber contactors (HFCs).

Solvent separated delipidated HDL may be delivered to staging sub-module 485 for delivery through delivery port 455 into the delivery cannula 450 to a treatment site. In one embodiment, system 400 also includes adjuvant module 490. Adjuvant module may contain an adjuvant such as Apo A1 or a mutant form thereof. Alternatively or additionally, adjuvant module 490 may include additional treatment agents, such as cellular components and drugs that may be beneficial to treating, for example, atherosclerotic plaque.

The embodiment shown in FIG. 4 describes a continuous loop system where blood is withdrawn and delipidated plasma, optionally with an adjuvant, is returned through the same catheter system. It is appreciated that there are many alternative catheter assemblies that may be utilized in such a system, including delivery catheters without balloons, delivery catheters with multiple balloons, delivery catheters with porous balloons, and the like catheter systems. The embodiments describe utilized separate withdrawal cannula and delivery cannula to describe a continuous configuration. It is also appreciated that multiple dedicated withdrawal/delivery cannulas are unnecessary. For example, in an embodiment of a catheter assembly similar to catheter assembly 405 but having an OTW configuration for a guidewire, the guidewire cannula may be used both to deliver the catheter assembly to a region of interest and to withdraw blood to the delipidation module or deliver plasma containing delipidated HDL to a treatment site. Representatively, once the catheter assembly is placed, the guidewire may be removed and the guidewire lumen may be connected to the delipidation module. A patient's blood may then be withdrawn to the delipidation module through the guidewire cannula.

Various formulations may have applicability to systemic infusion of a delipidated HDL formulation as well as local/catheter or stent/scaffold-based delivery of that formulation to enhance activation of pre-β-HDL and/or ATP-binding cassette protein A1 (ABCA1) mediated cholesterol and phospholid efflux in the wall of plaque.

In one embodiment, a formulation or composition is suitable to enhance the local pK of delipidated HDL into a blood vessel wall at a treatment site such as an atherosclerotic lesion or plaque. Enhancing the local pK will facilitate the microsolubilization pathway of lipid transfer for the lipid poor α-HDL or pre-β-HDL family or for Apo A1. A suitable formulation may contain a blood compatible viscosifier to, for example, enhance a residence time of the bioactive agent (e.g., delipidated HDL, pre-β-HDL, Apo A1) near a treatment site, such as near a plaque. Suitable viscosifiers include, but are not limited to, hyaluronic acid, polyvinylpyrrolidone (PVP), hydroxypropylmethacrylate (HPMA) copolymer systems, carboxymethyl cellulose (CMC). Representatively, delipidated HDL and/or other treatment agent may be combined in solution with a viscosifier to form a formulation or composition and the formulation may be introduced at a treatment site.

In another embodiment, a formulation or composition is selected that will stabilize the amphipathic helical structure of a lipid poor HDL family by providing a structure with one surface hydrophobic and the other hydrophilic. Examples include amphiphilic block-copolymers (e.g., poly(lactide) (PLA); poly(lactide)/polyglycolic, polylactic acid polyethylene glycol (PGLA-PEG) that will self assemble with lipid poor α-HDL or pre-β-HDL or Apo A1 or mutant form thereof. In another embodiment, biodegradable amphiphilic block-copolymers (e.g., PLA/PGLA-PEG, PLA/PGLA-dextrin) may be used to encapsulate the lipid poor α-HDL or pre-β-HDL family or Apo A1 or mutant form thereof to increase a residence time at a treatment site, or the stability in tissue, and/or to provide control release at a treatment site.

In another embodiment, a formulation or composition may contain an additive to enhance an interaction of lipid poor α-HDL or pre-β-HDL family or Apo A1. Representatively, a formulation may contain delipidated HDL and stearic acid or palmitic acid that will tend to improve the partitioning within a plaque (e.g., improve the uptake of HDL in the plaque). Such formulation may enhance the microsolubilization pathway. A hydrophobic component of stearic acid or palmitic acid may also be used to enhance the packaging of free cholesterol and phospholipids with lipid poor α-HDL or pre-β-HDL family or Apo A1. Such packaging will tend to decrease the disassociation constant, Km, enhance the rate of the efflux of cholesterol from a plasma membrane.

In another embodiment, a formulation or composition is designed to enhance the local pharmacokinetics of delipidated HDL. Enhancing the local pharmacokinetics of delipidated HDL will, in one embodiment, facilitate the aqueous diffusion pathway of lipid transport for a fully lipidated α-HDL particle. Representatively, in one embodiment, additives such as unsaturated phospholipids are combined with a formulation including delipidated α-HDL where the additive will tend to increase the free cholesterol and phospholipids solubility in the milieu of a fully lipidated α-HDL particle. The increased solubility will tend to increase a driving force gradient for diffusion into the α-HDL particle. The increased solubility also tends to increase a partitioning of free cholesterol and phospholipids into the milieu of fully lipidated α-HDL particle. In one embodiment, the additive or the additive formulation includes a molecule that, relative to other lumen sites, is specific for a site including an atherosclerotic plaque or lesion.

In another embodiment that increases the uptake of cholesterol in a reverse cholesterol transport pathway, a formulation or composition is provided of Apo A1 and a hydrophobic synthetic ligand. Representatively, the addition of a hydrophobic ligand, such as elastin pentapeptide, leucine-rich oligopeptide, stearoyl, olyeol, and/or palmitoyl group ligand will tend to enhance the binding of Apo A1 during the microsolubilization process. The presence of such ligand tends to enhance the diffusion of phospholipids during the aqueous diffusion pathway. The ligand may be bound, for example, to the amine or carboxyl terminus of Apo A1 and possibly may branch off one termini.

In another embodiment, a formulation or composition is provided that includes a cross-linker of Apo A1. In this embodiment, a cross-linked or ligated Apo A1 will tend to enhance the binding of Apo A1 during the microsolubilization process and may enhance the diffusion of phospholipids during the aqueous diffusion pathway. Suitable cross-linking agents of Apo A1 include, but are not limited to, natural or synthetic aldehydes such as lysoylperoxidate, gennicin, and reuterin.

In another embodiment, a formulation or composition may be introduced that has a property that will enhance a conversion of α-HDL into Apo A1 or pre-β-HDL without the need of solvent processing. In such case, a treatment agent will selectively target α-HDL and enhance the regeneration rate of Apo A1. In one embodiment, α-HDL may be contacted with an aqueous suspension of cholesterol or lipid micelle that will tend to drive the equilibrium toward the cholesterol or lipid micelle and delipidate α-HDL. Alternatively, this formulation or composition can be designed to be a triggered component by an external method such as photodynamic therapy (PDT).

In another embodiment, a formulation or composition may have a property that will tend to enhance the efficiency of lipid poor α-HDL or pre-β-HDL, or Apo A1 (in synthetic or native forms) by effecting their co-receptors, or biological pathways involved in delipidation and cholesterol transport. Such a formulation may be locally or locally delivered into an arterial tree by stent or other implantable scaffolds or catheters. Representatively, a mutant or mimic of Apo A1 peptide may be co-formulated with a treatment agent. Representatively, the treatment agent may have a property that will selectively increase the ABCA1 transporter expression in macrophages, for example, LXR agonist. LXR receptors are the membrane of the nuclear hormone receptor superfamily. The sterol-responsive transcription factors regulate the expression of a number of genes involved in intestinal cholesterol absorption, conversion of cholesterol to bile acids, and release cholesterol transport. Activation of LXR tends to block cholesterol absorption and induce cholesterol efflux from lipid-loaded cells such as macrophages. Because increased cholesterol efflux is protected to limit the transformation of macrophages into atherosclerotic foam cells, LXR activity is predicted to be anti-atherogenic. In another embodiment, a treatment agent is selected that will stabilize ABCA1 by tending to protect it from thiol protease-mediated degradation (e.g., in small molecule which prevents degradation of calpain).

In addition to delipidated HDL, reverse cholesterol transport may be facilitated by HDL-mimicking peptides, such as amphiphatic helical peptides including those described by Segrest, J. P., et al. (1992) *J. Lipid Res.*, 33, 141-66, designated 18A, 37pA, and 18Ac-18A-N8$_2$. Cyclodextrins have also been shown to remove cholesterol from cell membranes in vitro and therefore, in another embodiment, may be introduced systemically or locally at a treatment site, such as at a location adjacent an atherosclerotic plaque.

Various devices may be used to deliver delipidated HDL, HDL-mimicking peptides, cyclodextrins, or any of the various formulations or treatment agents described above. These devices include, but are not limited to, local catheter or stent/scaffold-based delivery devices. FIG. 3 and FIG. 4 illustrated suitable devices in the context of therapy system that delipidate HDL and/or deliver delipidated HDL and/or other agents (including, for example, HDL-mimicking peptides and cyclodextrins). FIGS. 5-9 describe additional devices that are also suitable to the blood stream.

Figure 5:
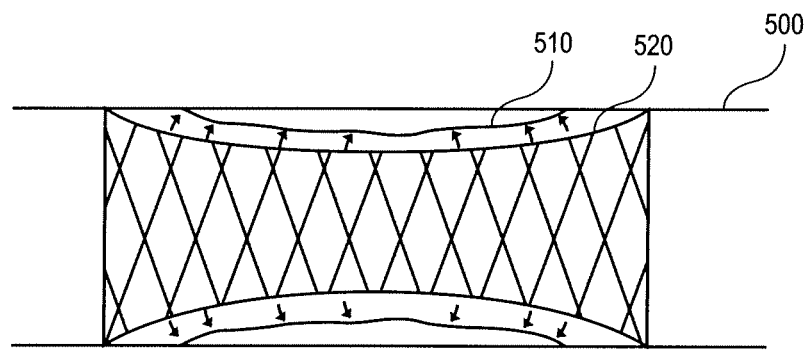
FIG. 5 shows a schematic cross-sectional side view of a stent in a blood vessel.

FIG. 5 shows an embodiment of a scaffold or stent placed in a region of a blood vessel including a lesion, such as atherosclerotic plaque. FIG. 5 shows blood vessel 500 including lesion 510 with stent 520 deployed in the area of plaque 510. In one embodiment, a prior procedure, such as a percutaneous transluminal coronary angioplasty (PTCA) procedure may have been performed to open blood vessel 500 at the area of plaque 510. Stent 520 may have subsequently been deployed in the blood vessel.

In one embodiment, stent 520 is composed of a metal, an alloy, a polymer, or a combination thereof and cholesterol-absorbing carrier molecules included in a stent coating or in the body of the stent. Examples of materials used to form stents include, but are not limited to, ELATINITEL®, nitinol (nickel-titanium alloy), stainless steel, tantalum, tantalum-based alloys, platinum, platinum-based alloys, and other metals and their alloys. Alternatively, stent 520 is composed of a bioabsorbable polymer or biostable polymer. A polymer or coating is "bioabsorable" or "biodegradable" when it is capable of being completely or substantially degraded or eroded when exposed to either an in vivo environment or an in vitro environment having physical, chemical, or biological characteristics substantially similar to those of the in vivo environment within a mammal. A polymer or coating is "degradable or erodable" when it can be gradually broken down, resorbed, absorbed and eliminated by, for example, hydrolysis, enzymolysis, metabolic processes, bulk or surface erosion, and the like within a mammal. It is to be appreciated that traces of residue of polymer may remain following biodegradation. A "biostable" polymer is a polymer that is not bioabsorbable.

Suitable polymers used in embodiments of a material for stent 520, include, but are not limited to, hydrophobic, hydrophilic, ampiphilic, biodegradable, or a combination thereof. Examples of hydrophobic polymers include, but are not limited to, poly (ester amide), polystyrene-polisobutylene-polystyrene block copolymer (SIS), polystyrene, polyisobutylene, polycaprolactone, poly (L-lactide), poly (D,L-lactide), polylactic acid (PLA), poly (lactide-co-glycolide), poly (glycolide), polyalkylene, polyfluoroalkylene, polyhydroxyalkanoate, poly (3-hydroxybutyrate), poly (4-hydroxybutyrate), poly (3-hydroxyvalerate), poly (3-hydroxybutyrate-co-3-hydroxyvalerate), poly (3-hydroxyhexanoate), poly (4-hydroxyhexanoate), mid-chain polyhydroxyalkanoate, poly (trimethylene carbonate), poly (orthoester), polyphosphazene, poly (phosphoester), poly (tyrosine derived arylates), poly (tyrosine derived carbonates), polydimethyloxanone (PDMS), polyvinylidene fluoride (PVDF), polyhexafluoropropylene (HFP), polydimethylsiloxane, poly (vinylidene fluoride-co-hexafluoropropylene (PVDF-HFP), poly (vinylidene fluoride-co-chlorotrifluoroethylene) (PVDF-CTFE), poly (butyl methacrylate), poly(methyl mathacrylate), poly (vinyl acetate) (PVA), poly (ethylene-co-vinyl acetate), poly (ethylene-co-vinyl alcohol), poly (ester-urethane), poly (ether-urethane), poly (carbonate-urethane), poly (silicone-urethane), poly (2-hydroxyethyl methacrylate), SOLEF® polyvinylidene fluoride (PVDF), poly (urea-urethane), and combinations thereof.

Examples of hydrophilic polymers include, but are not limited to, polymers and co-polymers of hydroxyethly methacrylate (HEMA); poly(methyl methacrylate) (PMMA); poly (ethylene glycol) acrylate (PEGA); PEG methacrylate; phosphorylcholine; 2-methacryloyloxyethyl phosphorylcholine (MPC); n-vinyl pyrrolidone (VP); carboxylic acid bearing monomers such as methacrylic acid (MA), acrylic acid (AA); hydroxyl bearing monomers such as HEMA, hydroxypropyl methacrylate (HPMA), hydroxypropylmethacrylamide, alkoxymethacrylate, alkoxyacrylate, and 3-trimethylsilyl-propyl methacrylate (TMSPMA), poly (ethylene glycol) (PEG), poly (propylene glycol) (PPG), SIS-PEG-polystyrene-PEG, polisobutylene-PEG, PCL-PEG, PLA-PEG, PMMA-PEG, PDMS-PEG, PVD-PEG, PLURONIC® surfactants (poly-propylene oxide-co-polyethylene glycol), poly (tetramethylene glycol), hydroxyfunctinal poly (vinyl pyrrolidone), polyalkylene oxide, dextran, detrin, sodium hyaluronate, hyaluronic acid, heparin, elastin, chitosan; and combinations thereof.

Examples of biodegradable polymers include, but are not limited to, polymers having repeating units such as, for example, an α-hydroxycarboxylic acid, a cyclic diester of an α-hydroxycarboxylic, a dioxanone, a lactone, a cyclic carbonate, a cyclic oxalate, an epoxide, a glycol, an anhydride, a lactic acid, a glycolic acid, a clycolic acid, a lactide, a glycolide, an ethylene oxide, an ethylene glycol, or combinations thereof.

In some embodiments, the biodegradable polymers include, but are not limited, to polyesters, polyhydroxyalkanoates (PHAs), poly (ester amides), amino acids, PEG and/or alcohol groups, polycaprolactones, poly (L-lactide), poly (D,L-lactide, poly (D,L-lactide-co-PEG) block copolymers, poly (D,L-lactide-co-trimethylene carbonate), polyglycolides, poly (lactide-co-glycolide), polydioxanones, polyorthoesters, polyahydrides, poly (glycolic acid-co-trimethylene carbonate), polyphosphoesters, polyphosphoester urethans, poly (amino acids), polycyanoacrylates, poly(trimethylene carbonate), poly (imino carbonate), polycarbonates, polyurethanes, copoly (ether-esters) (e.g., PEO/PLA), polyakylene oxalates, polyphosphazenes, PHA-PEG, and any derivatives, analogs, homologues, salts, copolymers and combinations thereof.

Cholesterol transport molecules such as HDL or analogs thereof or cyclodextrins may be included in a stent coating on stent 520 or included in the body of stent 520 such as, for example, a biodegradable polymeric stent. The release profile of the cholesterol-absorbing carrier molecules can be controlled by tailoring the chemical composition and crystallinity of the coating or the bioabsorbable stent material (e.g., the more crystalline the slower the release rate). It is appreciated that in addition to the delivery of cholesterol-absorbing molecules, the stent may be coated or be formed to include other bioactive agents that may similarly be released from the stent or biobeneficial agents that provide a biologic benefit without being released from the stent.

FIG. 5 shows stent 520 placed over plaque 510. In another embodiment, stent 520 may be placed upstream in vessel 500 (e.g., plaque free portion of blood vessel 500). In this manner, the release of cholesterol transport molecules from stent 520 will be transported by circulating blood downstream toward plaque 510.

Figure 6:
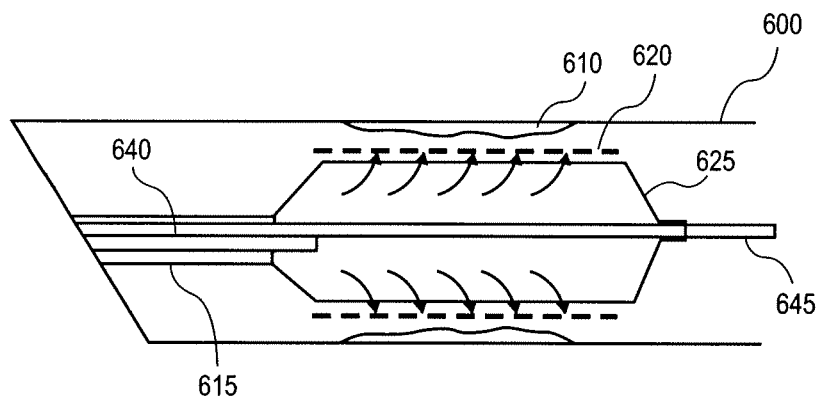
FIG. 6 shows a schematic cross-sectional side view of a catheter assembly in a blood vessel.
Figure 6:
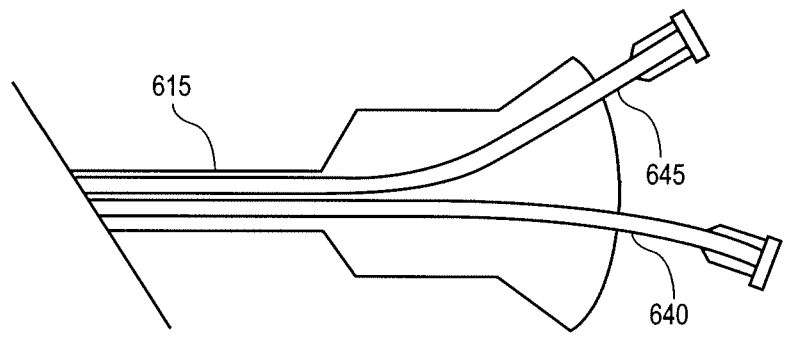

In another embodiment, cholesterol transport molecules or other agents may be delivered locally in combination with stent delivery (e.g., at the time of stent delivery or at a time thereafter). FIG. 6 shows a catheter assembly within a blood vessel. In this embodiment, blood vessel 600 includes lesion 610 such as atherosclerotic plaque. A catheter assembly including balloon 625 is positioned in blood vessel 600 with the balloon at a position adjacent plaque 610. In this embodiment, balloon 625 is shown partially expanded and shown carrying, or acting as a carrier of stent 620. In one embodiment, balloon 625 may be inflated sufficient to place stent 620 against the wall of blood vessel 600, possibly at a position enveloping plaque 610 or at a position proximal to plaque 610. A proximal end or skirt of balloon 625 is connected to a distal end of primary cannula or tube 615 that is, for example, percutaneously, transluminally inserted through, for example, a femoral or radial artery. Primary cannula 615 has a lumen therethrough that includes guidewire cannula 645 (extending in an over-the-wire (OTW) fashion through balloon 625) and inflation cannula 640.

In the embodiment shown in FIG. 6, balloon 625 may be porous so that a bioactive agent such as or including cholesterol transport molecules may be delivered through pores in the working length of porous balloon 625. Representatively, balloon 625 may be a perfusion balloon of an elastomeric material such as nylon, PEBAX, polyurethanes, or PET with microholes to deliver the bioactive agent. Representatively, microholes may have a diameter on the order of one micron 100 microns. Alternatively, porous balloons constructed from extended polytetrafluoroetylene (ePTFE) such as an EASY STREET® balloon and ultra high molecular weight polyethylene (UHMWPE) with node and fibril structure can be used as a suitable material for balloon 625. Balloon 625 may be thermally bonded to primary cannula 615. Inflation cannula 640 extends from a proximal point exterior to a patient receiving the catheter and a distal end within balloon 625. In this embodiment, a solution containing the bioactive agent(s) is delivered through inflation cannula 640 to inflate balloon 625 and deliver the bioactive agent(s) into blood vessel 600. In one embodiment, balloon 625 is made of a porous material such as ePTFE. A suitable pore size for an ePTFE balloon material is on the order of one micron to 60 microns. The porosity of ePTFE material can be controlled to accommodate a bioactive agent, flow rate or particle size by changing a microstructure of an ePTFE tape used to form a balloon, for example, by wrapping around a mandrel. Alternatively, pore size can be controlled by controlling the compaction process of the balloon or by creating pores (e.g., micropores) using a laser.

Figure 7:
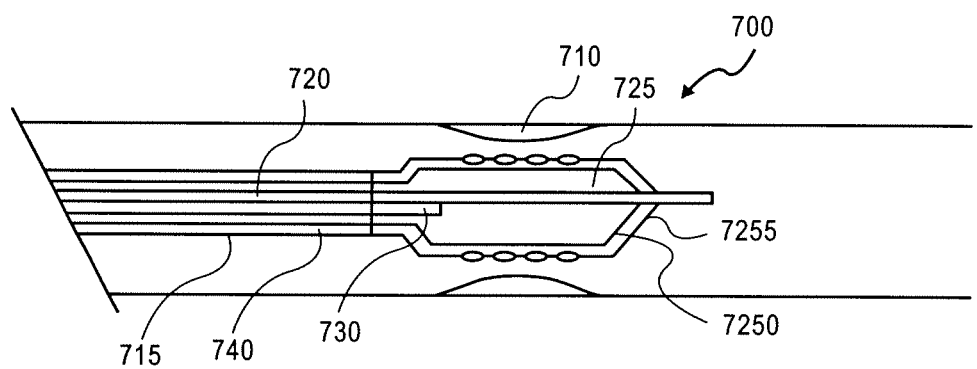
FIG. 7 shows a schematic cross-sectional side view of another embodiment of a catheter assembly in a blood vessel.
Figure 7:
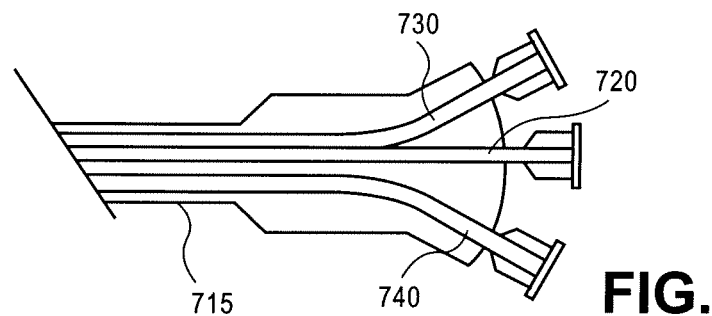

FIG. 7 shows another embodiment of a catheter assembly. The catheter assembly, in this embodiment, includes a porous balloon through which an agent, such as a cholesterol transport molecule may be introduced. FIG. 7 shows the catheter assembly disposed within blood vessel 700. The catheter assembly has a porous balloon configuration positioned at treatment site 710. The catheter assembly includes primary cannula 715 having a length that extends from a proximal end of the catheter assembly (e.g., located external to a patient during a procedure) to connect with a proximal end or skirt of balloon 725. Primary cannula 715 has a lumen therethrough that includes inflation cannula 730. Inflation cannula 730 extends from a proximal end of the catheter assembly to a point within balloon 725. Inflation cannula 730 has a lumen therethrough allowing balloon 725 to be inflated through inflation cannula 730.

The catheter assembly also includes guidewire cannula 720 extending, in this embodiment, through balloon 725. Guidewire cannula 720 has a lumen therethrough sized to accommodate a guidewire. No guidewire is shown within guidewire cannula 720. The catheter assembly may be an over-the-wire (OTW) configuration or rapid exchange (RX) type catheter assembly. FIG. 7 illustrates an OTW type catheter assembly.

The catheter assembly shown in FIG. 7 also includes delivery cannula 740. In this embodiment, delivery cannula 740 extends from a proximal end of the catheter assembly to proximal end or skirt of balloon 725. Balloon 725 is a double layer balloon. Balloon 725 includes inner layer 7250 that is a non-porous material, such as PEBAX, Nylon or PET. Balloon 725 also includes outer layer 7255. Outer layer 7255 is a porous material, such as extended polytetrafluoroethylene (ePTFE). In one embodiment, delivery cannula 740 is connected to between inner layer 7250 and outer layer 7255 so that a treatment agent can be introduced between the layers and permeate through pores in balloon 725 into a lumen of blood vessel 700.

As illustrated in FIG. 7, in one embodiment, the catheter assembly is inserted into blood vessel 700 so that balloon 725 is aligned with treatment site 710. In another embodiment, balloon 725 may be positioned upstream (e.g., proximal) to treatment site 710. Following alignment of balloon 725 of the catheter assembly, balloon 725 may be inflated by introducing an inflation medium (e.g., liquid through inflation cannula 730). In one embodiment, balloon 725 is only partially inflated or has an inflated diameter less than an inner diameter of blood vessel 700 at treatment site 710. In this manner, balloon 725 does not contact or only minimally contacts the blood vessel wall. A suitable expanded diameter of balloon 725 is on the order of 2.0 to 5.0 millimeters (mm) for coronary vessels. It is appreciated that the expanded diameter may be different for peripheral vasculature. Following the expansion of balloon 725, one or more agents, including a cholesterol transport molecule is introduced into delivery cannula 740. The agent(s) flow through delivery cannula 740 into a volume between inner layer 7250 and outer layer 7255 of balloon 725. At a relatively low pressure (e.g., on the order of two to four atmospheres (atm)), the agent(s) then permeate through the pores of outer layer 7255 into blood vessel 700.

Figure 8:
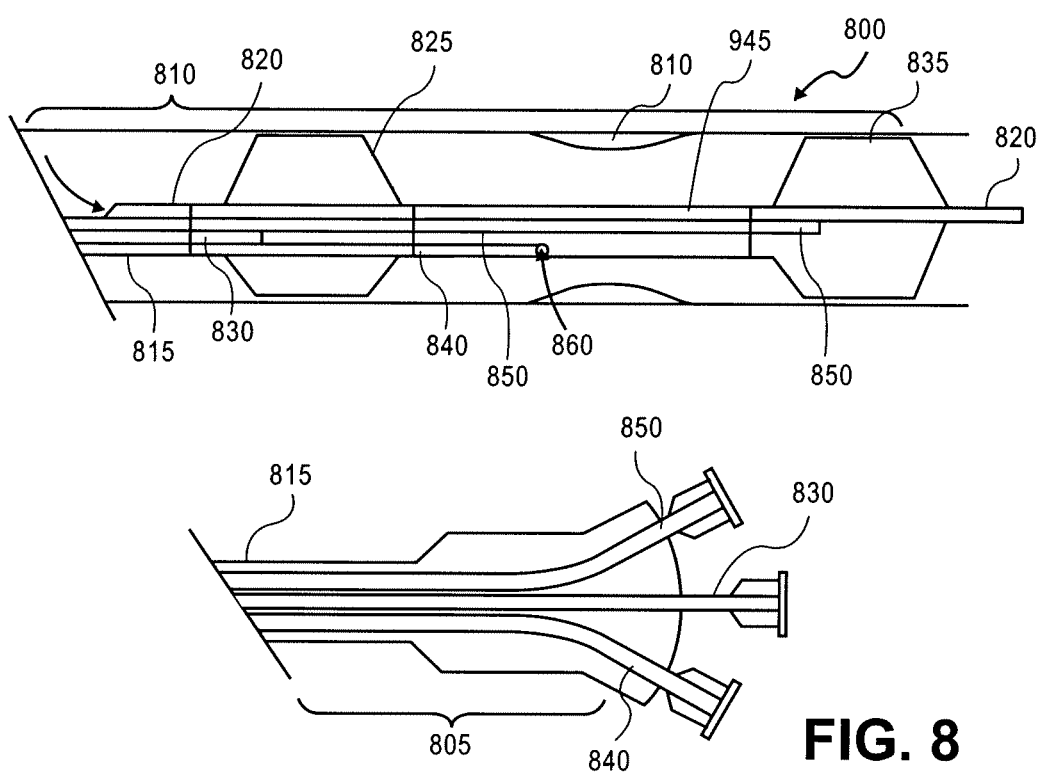
FIG. 8 shows a schematic cross-sectional side view of another embodiment of a catheter assembly in a blood vessel.

FIG. 8 shows an embodiment of a catheter assembly having two balloons where one balloon is located proximal to treatment site 810 and a second balloon is located distal to treatment site 810. FIG. 8 shows the catheter assembly disposed within blood vessel 800. The catheter assembly has a tandem balloon configuration including proximal balloon 825 and distal balloon 835 aligned in series at a distal portion of the catheter assembly. The catheter assembly also includes primary cannula 815 having a length that extends from a proximal end of the catheter assembly 800 (e.g., located external to a patient during a procedure) to connect with a proximal end or skirt of balloon 825. Primary cannula 815 has a lumen therethrough that includes inflation cannula 830 and inflation cannula 850. Inflation cannula 830 extends from a proximal end of catheter assembly 800 to a point within balloon 825. Inflation cannula 830 has a lumen therethrough allowing balloon 825 to be inflated through inflation cannula 830. In this embodiment, balloon 825 is inflated through an inflation lumen separate from the inflation lumen that inflates balloon 835. Inflation cannula 850 has a lumen therethrough allowing fluid to be introduced in the balloon 835 to inflate the balloon. In this manner, balloon 825 and balloon 835 may be separately inflated. Each of inflation cannula 830 and inflation cannula 850 extends from, in one embodiment, the proximal end of the catheter assembly through a point within balloon 825 and balloon 835, respectively.

The catheter assembly also includes guidewire cannula 820 extending, in this embodiment, through each of balloon 825 and balloon 835 through a distal end of catheter assembly. Guidewire cannula 820 has a lumen therethrough sized to accommodate a guidewire. No guidewire is shown within guidewire cannula 820. The catheter assembly may be an over the wire (OTW) configuration or a rapid exchange (RX) type catheter assembly. FIG. 8 illustrates an RX type catheter assembly.

The catheter assembly in FIG. 8 also includes delivery cannula 840. In this embodiment, delivery cannula 840 extends from a proximal end of the catheter assembly through a location between balloon 825 and balloon 835. Secondary cannula 845 extends between balloon 825 and balloon 835. A proximal portion or skirt of balloon 835 connects to a distal end of secondary cannula 845. A distal end or skirt of balloon 825 is connected to a proximal end of secondary cannula 845. Delivery cannula 840 terminates at opening 860 through secondary cannula 845. In this manner, an agent such as a cholesterol transport carrier molecule may be introduced between balloon 825 and balloon 835 positioned between treatment site 710.

FIG. 8 shows balloon 825 and balloon 835 each inflated to occlude a lumen of blood vessel 800 and isolate treatment site 810. In one embodiment, each of balloon 825 and balloon 835 are inflated to a point sufficient to occlude blood vessel 800 prior to the introduction of a treatment agent. An agent such as a cholesterol transport molecule is then introduced.

In the above embodiment, separate balloons having separate inflation lumens are described. It is appreciated, however, that a single inflation lumen may be used to inflate each of balloon 825 and balloon 835. Alternatively, in another embodiment, balloon 835 may be a guidewire balloon configuration such as a PERCUSURG™ catheter assembly where the catheter assembly including only balloon 825 is inserted over a guidewire including balloon 835.

Figure 9:
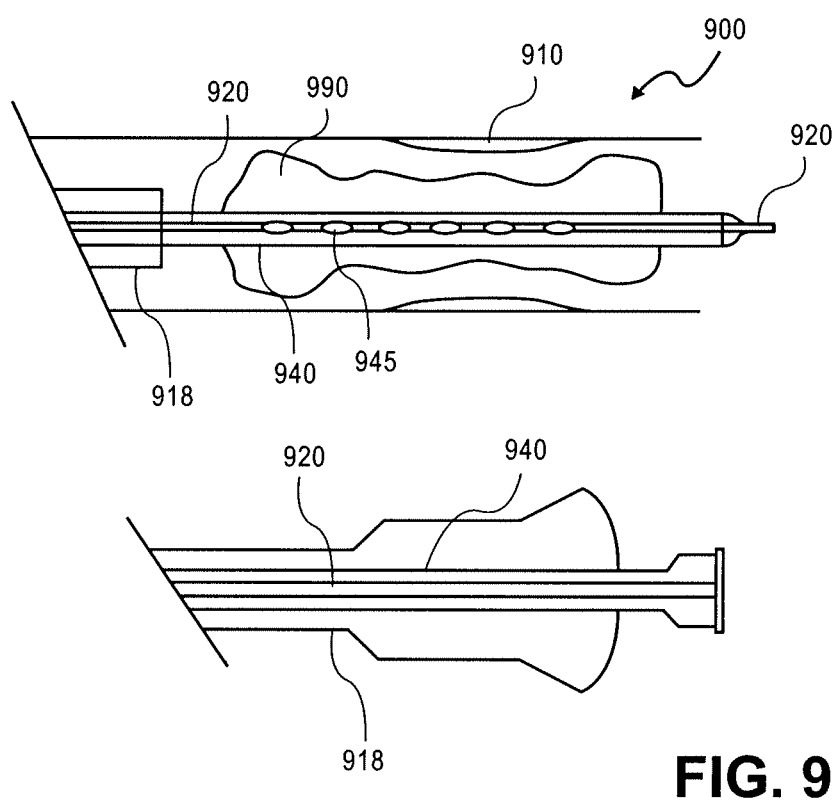
FIG. 9 shows a schematic cross-sectional side view of another embodiment of a catheter assembly in a blood vessel.

FIG. 9 shows another embodiment of a catheter assembly suitable for introducing an agent(s) at a treatment site. FIG. 9 shows a catheter assembly disposed within blood vessel 900. In this embodiment, the catheter assembly utilizes an absorbent possibly porous device such as a sponge or a brush, connected to a catheter to dispense an agent(s).

In one embodiment, the catheter assembly illustrated in FIG. 9 includes guidewire cannula 920 extending from a proximal end of the catheter assembly (e.g., external to a patient during a procedure) to a point in blood vessel 900 beyond treatment site 910. Overlying guidewire cannula 920 is primary cannula 940. In one embodiment, primary cannula 940 has a lumen therethrough of a diameter sufficient to accommodate guidewire cannula 920 and to allow an agent to be introduced through primary cannula 940 from a proximal end to a treatment site. In one embodiment, the catheter assembly includes a brush or sponge material connected at a distal portion of primary cannula 940. A sponge is representatively shown. Sponge 990 has an exterior diameter that, when connected to an exterior surface of primary cannula 940 will fit within a lumen of blood vessel 900. The catheter assembly also includes retractable sheath 918 overlying primary cannula 940. During insertion of the catheter assembly into a blood vessel to a treatment site, sponge 990 may be disposed within sheath 918. Once a distal portion of the catheter assembly is disposed at a treatment site, sheath 918 may be retracted to expose sponge 990. FIG. 9 shows sheath 918 retracted, such as by pulling the sheath in a proximal direction.

In one embodiment, prior to insertion of the catheter assembly in FIG. 9, sponge 990 may be loaded with one or more agents. Representatively, sponge 990 may be loaded with a solution including a cholesterol transport molecule.

In one embodiment, the catheter assembly of FIG. 9 may provide for additional introduction of a bioactive agent through primary cannula 940. FIG. 9 shows primary cannula 940 having a number of dispensing ports 945 disposed in series along a distal portion of primary cannula 940 coinciding with a location of sponge 990. In this manner, once sponge 990 is placed at treatment site 910 within blood vessel 900, additional bioactive agent may be introduced through primary cannula 940 if desired.

In the above embodiments, many references are made to releasing an agent into a blood vessel by way of a stent/scaffold or catheter delivery. Suitable agents include delipidated HDL, HDL-mimicking peptides, cyclodextrins, and/or any of the various formulations or treatment agents described above. In another embodiment, a device may be inserted for the purpose of providing receptors to capture/absorb cholesterol that is released from a blood vessel by, for example, the aqueous diffusion pathway. In one embodiment, such a device may include a catheter having a distal end, possibly with a balloon, where a surface of a distal portion (e.g., a surface of a working length of a balloon) is coated with a composition or membrane that is receptive to cholesterol. As cholesterol is diffused from a cell membrane in the aqueous diffusion's pathway, the cholesterol is captured/absorbed by the coating/membrane of the catheter device.

In still another embodiment, rather than delivering an agent, such as a cholesterol transport or absorbing molecule to a blood vessel or delivering a device to the blood vessel with a coating/membrane to capture/absorb cholesterol, an embodiment contemplates injection of cholesterol-absorbing molecules directly into a wall of a blood vessel such as, for example, by a needle catheter. FIG. 10 illustrates an embodiment of a delivery apparatus for delivering a bioactive agent, such as a cholesterol-absorbing molecule (e.g., a delipidated HDL), to or through a desired area of a blood vessel (a physiological lumen) or tissue to a localized area of the blood vessel or a localized area of tissue possibly located adjacent to the blood vessel, for example, in a periadventitial space. The delivery apparatus is similar in certain respects to the delivery apparatus described in commonly-owned, U.S. patent application Ser. No. 09/746,498 (filed Dec. 21, 2000), titled "Local Drug Delivery Catheter with Retractable Needle," of Steward et al. (now U.S. Pat. No. 6,692,466); U.S. patent application Ser. No. 10/394,834 (filed Mar. 20, 2003), titled "Drug Delivery Catheter with Retractable Needle," of Chow et al.; and U.S. patent application Ser. No. 10/749,354 (filed Dec. 31, 2003), titled "Needle Catheter." of Chan, et al. The delivery apparatus described is suitable, in one embodiment, for a percutaneous delivery of an agent where a desired form of the agent is introduced through a catheter needle.

Referring to FIG. 10, the delivery apparatus includes catheter assembly 1000. In one embodiment, catheter assembly 1000 is defined by elongated catheter body (cannula) 1012 having proximal portion 1013 and distal portion 1014. In one embodiment, proximal portion 1013 may reside outside a patient during a procedure while distal portion 1014 is placed at a region of interest, for example, within coronary blood vessel 1017.

Catheter assembly 1000 includes catheter body 1012 having a lumen therethrough extending from proximal portion 1013 to distal portion 1014. In this example, guidewire cannula 1016 is formed within catheter body 1012 for allowing catheter assembly 1000 to be fed and maneuvered over a guidewire (guidewire 1018 shown at this point within a lumen of guidewire cannula 1016). Guidewire cannula 1016 may extend from proximal portion 1013 to distal portion 1014, thus describing an over the wire (OTW) assembly. In another embodiment, typically described as a rapid exchange (RX) type catheter assembly, guidewire cannula 1016 extends only through a portion of catheter body 1012, for example, beginning and ending within distal portion 1014. An RX type catheter assembly is shown. It is appreciated that guidewire 1018 may be retracted or removed once catheter assembly 1000 is placed at a region of interest, for example, within a blood vessel (e.g., artery or vein).

In the embodiment of FIG. 10, catheter assembly 1000 includes balloon 1020 incorporated at distal portion 1014 of catheter assembly 1000. Balloon 1020 is an expandable body in fluid communication with inflation cannula 1028 disposed within catheter body 1012. Inflation cannula 1028 extends from balloon 1020 within distal portion 1014 through inflation port 1048 at proximal portion 1013 (e.g., at a proximal end of catheter assembly 1000). Inflation cannula 1028 is used to deliver a fluid to inflate balloon 1020.

In the embodiment shown in FIG. 10, balloon 1020 is in an expanded or inflated state that occludes blood vessel 1017. Balloon 1020 is selectively inflatable to dilate from a collapsed configuration to a desired or controlled expanded configuration. Balloon 1020 can be selectively inflated by supplying a fluid (e.g., liquid) into a lumen of inflation cannula 1028 at a predetermined rate of pressure through inflation port 1048. Likewise, balloon 1020 is selectively deflatable to return to a collapsed configuration or deflated profile.

In one embodiment, balloon 1020 can be defined by three portions: distal taper wall 1026, medial working length 1024, and proximal taper wall 1022. In one embodiment, proximal taper wall 1022 can taper at any suitable angle θ, typically between about 15° to less than about 90°, when balloon 1020 is in an expanded (inflated) configuration.

Balloon 1020 can be made from any suitable material, including, but not limited to, polymers and copolymers of polyolefins, polyamides, polyester and the like. The specific material employed should be compatible with inflation or expansion fluid and must be able to tolerate the pressures that are developed within balloon 1020. One suitable material is an elastomeric nylon such as PEBAX™, a condensation polymerized polyether block polyamide. Other suitable materials for balloon 1020 include, but are not limited to, a biocompatible blend of polyurethane and silicone, or a styrenic block copolymer (SBC) or blend of SBCs. Distal taper wall 1026, medial working length 1024, and proximal taper wall 1022 can be bound together by seams or be made out of a single seamless material. A wall of balloon 1020 (e.g., at any of distal taper wall 1026, medial working length 1024 and/or proximal taper wall 1022) can have any suitable thickness so long as the thickness does not compromise properties that are critical for achieving optimum performance.

Balloon 1020 may be inflated by the introduction of a fluid (e.g., liquid) into inflation cannula 1028 (through inflation port 1048 at a point outside a physiological lumen). Liquids containing therapeutic and/or diagnostic agents may be used to inflate balloon 1020. In one embodiment, balloon 1020 may be made of a material that is permeable to such therapeutic and/or diagnostic agents. To inflate balloon 1020, a suitable fluid may be supplied into inflation cannula 1028 at a predetermined pressure, for example, between about one and 20 atmospheres (atm). A specific pressure depends on various factors, such as the thickness of the balloon wall, the material of which balloon 1020 is made, the type of substance employed, and the flow rate that is desired.

Catheter assembly 1000, in the embodiment shown in FIG. 10 also includes delivery cannula 1030 and delivery cannula 1032 each connected to proximal taper wall 1022 of balloon 1020 and extending at a proximal end, in one embodiment, into a portion of catheter body 1012 of catheter assembly 1000. Representatively, a suitable length for delivery cannula 1030 and delivery cannula 1032 is on the order of three to 6.5 centimeters (cm). Delivery cannula 1030 and delivery cannula 1032 can be made from any suitable material, such as polymers and copolymers of polyamides, polyolefins, polyurethanes, and the like.

Catheter assembly 1000, in this view, also includes needle 1034 and needle 1036. Needle 1034 and needle 1036 extend from distal portion 1014 to proximal portion 1013 of catheter assembly 1000. At distal portion 1014, needle 1034 is slidably disposed through a lumen of delivery cannula 1030 and needle 1036 is slidably disposed through a lumen of delivery cannula 1032. Thus, a dimension of delivery cannula 1030 and delivery cannula 1032 are each selected to be such to allow a delivery device such as a needle to be moved therethrough. Representatively, delivery cannula 1030 has an inner diameter (lumen diameter) on the order of 0.002 inches to 0.020 inches (e.g., 0.0155 inches) and an outer diameter on the order of 0.006 inches to 0.05 inches (e.g., 0.0255 inches). FIG. 10 shows catheter assembly 1000 with each of needle 1034 and needle 1036 deployed in an extended configuration, i.e., extending from an end of delivery cannula 1030 and delivery cannula 1032, respectively. In a retracted configuration, the needles retract proximally into the delivery cannula lumens. Representatively, delivery cannula 1030 and delivery cannula 1032 may be spaced radially or circumferentially from each other, for example, between 45° and 180° apart.

FIG. 10 shows delivery cannula 1030 and delivery cannula 1032 each connected to an exterior surface of balloon 1020. Specifically, a distal end of each of delivery cannula 1030 and delivery cannula 1032 extend to a point equivalent to or less than a length of proximal taper wall 1022 of balloon 1020. One suitable technique for connecting delivery cannula 1030 or delivery cannula 1032 to balloon 1020 is through an adhesive. A suitable adhesive includes a cyanoacrylates (e.g., LOCTITE 414™) adhesive, particularly where the balloon material is a PEBAX™ material.

Catheter assembly 1000 in the embodiment shown in FIG. 10 also includes sheath ring 1025. Sheath ring 1025 is positioned over, in this embodiment, guidewire cannula 1016, inflation cannula 1028, delivery cannula 1030, and delivery cannula 1032, respectively. In one embodiment, sheath ring 1025 functions to inhibit delamination of the delivery cannulas from proximal taper wall 1022 of balloon 1020 and, where thermally sealed to the various cannulas may reduce the spacing (on a proximal side of sheath ring 1025) of the cannulas. Thus, a distal end of sheath ring 1025 is placed, in one embodiment, at a point immediately proximal to where a delivery cannula will rotate, bend or plicate in response to the expansion or inflation of balloon 1020. In one embodiment, sheath ring 1025 is a biocompatible material that is capable of connecting to (e.g., bonding to) a material for balloon 1020 and to a material for each of the noted cannulas that it surrounds. Representatively, a body of sheath ring 1025 has a length from a proximal end to a distal end on the order of 0.25 millimeters (mm) to 0.75 mm, such as 0.5 mm.

As noted above, each delivery cannula (e.g., delivery cannula 1030, delivery cannula 1032) folds up or bends distal to sheath ring 1025 with the inflation of balloon 1020. Thus, the path to be traveled by each needle (e.g., needle 1034 and needle 1036) crosses this bend or fold. To facilitate travel through a bend or folded region in each delivery cannula and to inhibit puncturing of the respective delivery cannula, each delivery cannula may include a deflector disposed along an interior wall. Representatively, a suitable deflector includes a ribbon of thin, generally flexible and generally resilient material (e.g., thickness on the order of about 0.0005 inches to about 0.003 inches and width on the order of about 0.005 inches and 0.015 inches). Suitable deflector materials, dimensions and connections within a catheter assembly are described in commonly-owned, U.S. patent application Ser. No. 09/746,498, filed Dec. 21, 2000 (now U.S. Pat. No. 6,692, 466); U.S. patent application Ser. No. 10/394,834, filed Mar. 20, 2003; and U.S. patent application Ser. No. 10/749,354, filed Dec. 31, 2003.

Referring again to FIG. 10, proximal portion 1013 of catheter assembly 1000 is intended, in one embodiment, to reside outside a patient while the remainder of catheter assembly 1000 is percutaneously introduced into, for example, the cardiovascular system of a patient via a brachial, a radial or a femoral artery. In this embodiment, proximal portion 1013 of catheter assembly 1000 includes hub 1040. A distal end of hub 1040 has an opening to accommodate a proximal end of catheter body 1012. Hub 1040 also has a number of cavities at least partially therethrough (extending in a distal to proximal direction) to accommodate needle 1034 and needle 1036, and inflation cannula 1028.

FIG. 10 shows a proximal end of needle 1034 and needle 1036 each connected (e.g., through an adhesive) to respective injection port 1044 and injection port 1046. In one embodiment, each injection port includes a luer fitting for syringe attachment. Each injection port allows for the introduction of a composition, including but not limited to a bioactive agent such as a cholesterol-absorbing molecule. It is appreciated that a composition introduced at injection portion 1044 and injection port 1046 may be the same or different. In this embodiment, inflation cannula 1028 terminates at the distal end of balloon inflation port 1048.

In one embodiment, catheter assembly 1000 also includes or can be configured to include an imaging assembly. Suitable imaging assemblies include ultrasonic imaging assemblies, optical imaging assemblies, such as an optical coherence tomography (OCT) assembly, magnetic resonance imaging (MRI).

In one embodiment, distal portion 1014 of catheter assembly 1000 is advanced to a region of interest in a blood vessel. Following placement, balloon 1020 is inflated through inflation cannula 1028 to a diameter approaching or similar to an interior diameter of blood vessel 1017. Thereafter, needle 1034 and/or needle 1036 is advanced into and/or through a wall of blood vessel to, for example, a periadventitial area. Following advancement of needle 1034 and/or needle 1036, one or more bioactive agents, such as a cholesterol-absorbing molecule, are introduced through needle 1034 and/or needle 1036 to the blood vessel or beyond a blood vessel.

In another embodiment, a catheter assembly such as catheter assembly 1000 may be used to co-introduce an agent such as a cholesterol transport molecule and a gel-forming biomaterial for enhanced retention of the bioactive agent. Representatively, a bioactive agent is delivered through needle 1034 while a gel-forming biomaterial is delivered through needle 1036. In one embodiment, needle 1034 and needle 1036 may be positioned closer together (e.g., 15° or less separation), rather than the 180° separation illustrated in FIG. 10. Suitable gel-forming biomaterial includes, but is not limited to, a thermosensitive gel material such as amphiphilic block copolymers, e.g., PEG-PLA, that may be introduced in the form of a liquid and gel in response to a body temperature. Alternatively, the gel material may be a pH sensitive material such as chitosan, which is soluble in aqueous solution of pH less than 6 but will precipitate into a gel at physiological pH, or a photoreactive gel, such as acrylate or methacrylate functionalized polymers, or amino acid oligomers functionalized by amine-conjugated phenyl azide groups, that may be introduced in the form of a liquid and gel in response to a light source. A suitable light source may be a light emitting diode or fiber optic bundle inserted through catheter assembly 1000, such as through guidewire cannula 1015 (after removal of guidewire 1018).

Another alternative for a gel material may be a two component gel such as sodium alginate and calcium chloride. The components of the two component gel may be introduced separately such as through a dual lumen needle or two separate needles. FIG. 11 shows a cross-section of an embodiment of needle 1036 that is a dual lumen needle. Needle 1036 includes lumen 1036A and lumen 1036B. Each of lumen 1036A and lumen 1036B may be supplied by a different delivery port so as not to contact the materials introduced through the separate lumens until they exit needle 1036.

In the preceding detailed description, reference is made to specific embodiments thereof. It will, however, be evident that various modifications and changes may be made thereto without departing from the broader spirit and scope of the following claims. The specification and drawings are, accordingly, to be regarded in an illustrative rather than a restrictive sense.

What is claimed is:

1. A method for treating a subject comprising:
   withdrawing an amount of blood from the subject using a catheter assembly;
   delipidating high density lipoprotein (HDL) present in the amount of blood, wherein delipidating comprises combining the amount of blood with a solvent and a surfactant;

adding a surface coating to the delipidated HDL for increasing a partition coefficient of the delipidated HDL; and after delipidating, (1) combining an exogenous bioactive agent having a hydrophobic ligand bound thereto with the delipidated HDL with the surface coating, wherein the exogenous bioactive agent includes at least one of an apolipoprotein A1 (Apo A1), a functional Apo A1 mutant, and a functional Apo A1 mimetic peptide, and (2) forming a composition comprising (i) the delipidated HDL with the surface coating combined with the exogenous bioactive agent having a hydrophobic ligand bound thereto, and (ii) a viscosifier including at least one of hyaluronic acid, polyvinylpyrrolidone (PVP), a hydroxypropylmethacrylate (HPMA) copolymer system, and carboxymethyl cellulose (CMC); and introducing the composition into a blood stream or tissue of the subject, using the catheter assembly.

2. The method of claim 1, wherein introducing comprises systemically introducing.

3. The method of claim 1, wherein introducing comprises locally introducing.

4. The method of claim 1, wherein introducing comprises locally introducing to an ischemic area.

5. The method of claim 1, wherein introducing comprises introducing the delipidated HDL upstream from a treatment site.

6. The method of claim 1, wherein introducing comprises introducing to a periadventitial area.

7. The method of claim 6, further comprising introducing a gel-forming biomaterial to the periadventitial area.

8. The method of claim 1, wherein withdrawing, delipidating and introducing comprise a closed loop system.

9. The method of claim 1, wherein the hydrophobic ligand is selected from the group consisting of an elastin pentapeptide, leucine-rich oligopeptide, stearoyl, olyeol and palmitoyl.

10. The method of claim 1 wherein the surfactant is selected from the group consisting of a sulfate, a sulfonate, a phosphate, a carboxylate and a sulfosuccinate.

11. A method for treating a subject comprising:

delivering to a treatment site within a lumen of a blood vessel of the subject, in a wall of the blood vessel of the subject, or periadvential area beyond the blood vessel by a percutaneous transluminal route, a composition comprising (i) a delipidated HDL and an exogenous bioactive agent having a hydrophobic ligand bound thereto, the delipidated HDL comprising an added surface coating having a property that increases a partition coefficient of the delipidated HDL into the treatment site, and (ii) a viscosifier, wherein the delivering step comprises locally delivering by placing a stent within the blood vessel of the subject, wherein the stent comprises the composition as a coating on a body of the stent or as a portion of the body of the stent, and wherein the viscosifier comprises at least one of hyaluronic acid, polyvinylpyrrolidone (PVP), a hydroxypropylmethacrylate (HPMA) copolymer system, and carboxymethyl cellulose (CMC), and wherein the exogenous bioactive agent includes at least one of an apolipoprotein A1 (Apo A1), a functional Apo A1 mutant, and a functional Apo A1 mimetic peptide.

12. The method of claim 11, wherein prior to delivering the agent, the method comprises:

occluding the blood vessel at a point upstream of a treatment site and a point downstream of the treatment site.

13. The method of claim 11, wherein prior to delivering the delipidated HDL, the method further comprises at least partially occluding the blood vessel at a treatment site with a porous occlusion device, and delivering comprises delivering the agent through the porous occlusion device.

14. The method of claim 11, wherein prior to delivering the agent, the method comprises inserting an occlusion device into the blood vessel that at least partially occludes the blood vessel, and delivering comprises delivering the agent through the occlusion device.

15. The method of claim 14, wherein the occlusion device comprises a balloon assembly comprising a porous portion and delivering comprises delivering the one of the agent through the porous portion.

16. The method of claim 14, wherein the occlusion device comprises a sponge.

17. The method of claim 11, wherein the treatment site comprises a periadventitial area.

18. The method of claim 17, further comprising introducing a gel biomaterial to the periadvential area.

* * * * *